US011211169B2

(12) United States Patent
Dey et al.

(10) Patent No.: US 11,211,169 B2
(45) Date of Patent: *Dec. 28, 2021

(54) FINDING PRECISE CAUSAL MULTI-DRUG-DRUG INTERACTIONS FOR ADVERSE DRUG REACTION ANALYSIS

(71) Applicant: International Business Machines Corporation, Armonk, NY (US)

(72) Inventors: Sanjoy Dey, White Plains, NY (US); Mohamed Ghalwash, Yorktown Heights, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 240 days.

This patent is subject to a terminal disclaimer.

(21) Appl. No.: 16/176,022

(22) Filed: Oct. 31, 2018

(65) Prior Publication Data

US 2019/0279775 A1 Sep. 12, 2019

Related U.S. Application Data

(63) Continuation of application No. 15/913,221, filed on Mar. 6, 2018.

(51) Int. Cl.
 *G16H 70/40* (2018.01)
 *G16H 50/70* (2018.01)
 *G06N 5/02* (2006.01)

(52) U.S. Cl.
 CPC ............ *G16H 70/40* (2018.01); *G06N 5/025* (2013.01); *G16H 50/70* (2018.01)

(58) Field of Classification Search
 CPC ... G06F 1/00–2221/2153; G16H 10/00–80/00; G06N 3/00–99/007
 See application file for complete search history.

(56) References Cited

U.S. PATENT DOCUMENTS

2005/0015278 A1 1/2005 Ghouri
2008/0147441 A1 6/2008 Kil
(Continued)

FOREIGN PATENT DOCUMENTS

WO WO03/021389 A2 3/2003

OTHER PUBLICATIONS

List of IBM Patents or Patent Applications Treated as Related, Oct. 2, 2018, 2 pages.
(Continued)

*Primary Examiner* — Elaine Gort
*Assistant Examiner* — Jonathon A. Szumny
(74) *Attorney, Agent, or Firm* — Stephen J. Walder, Jr.; William J. Stock

(57) ABSTRACT

Mechanisms are provided for implementing a framework to learn multiple drug-adverse drug reaction associations. The mechanisms receive and analyze patient electronic medical record data and adverse drug reaction data to identify co-occurrences of references to drugs with references to adverse drug reactions (ADRs) to thereby generate candidate rules specifying multiple drug-ADR relationships. The mechanisms filter the candidate rules to remove a subset of one or more rules having confounder drugs specified in the subset of one or more candidate rules, and thereby generate a filtered set of candidate rules. The mechanisms further generate a causal model based on the filtered set of candidate rules. The causal model comprises, for each ADR in a set of ADRs, a corresponding set of one or more rules, each rule specifying a combination of drugs having a causal relationship with the ADR.

14 Claims, 6 Drawing Sheets

(56) References Cited

U.S. PATENT DOCUMENTS

| | | | |
|---|---|---|---|
| 2012/0209625 A1* | 8/2012 | Armstrong | G06F 19/326 705/3 |
| 2013/0144636 A1* | 6/2013 | Pouliot | G06F 19/326 705/2 |
| 2013/0179375 A1 | 7/2013 | Tatonetti et al. | |
| 2013/0226616 A1* | 8/2013 | Nigam | G16H 70/60 705/3 |
| 2014/0095201 A1* | 4/2014 | Farooq | G16H 50/30 705/3 |
| 2014/0236630 A1* | 8/2014 | Murata | G06Q 50/22 705/3 |
| 2015/0324693 A1 | 11/2015 | Hu et al. | |
| 2016/0048655 A1 | 2/2016 | Maitra et al. | |
| 2016/0092793 A1 | 3/2016 | Garrow et al. | |
| 2017/0083670 A1 | 3/2017 | Kosaka et al. | |
| 2017/0116390 A1 | 4/2017 | Fokoue-Nkoutche et al. | |
| 2017/0316175 A1 | 11/2017 | Hu | |
| 2018/0004902 A1 | 1/2018 | Aronow et al. | |
| 2018/0068089 A1 | 3/2018 | Hu et al. | |
| 2018/0308569 A1* | 10/2018 | Luellen | G16H 40/20 |
| 2019/0005019 A1 | 1/2019 | Burke et al. | |
| 2019/0279757 A1 | 9/2019 | Hanina et al. | |
| 2019/0392955 A1 | 12/2019 | Israeli | |

OTHER PUBLICATIONS

Allen, Corville O. et al., "Medical Condition Independent Engine for Medical Treatment Recommendation System", filed Sep. 12, 2016, U.S. Appl. No. 15/262,311.

Du, L et al., "Graphic Mining of High-Order Drug Interactions and Their Directional Effects on Myopathy Using Electronic Medical Records", CPT Pharmacometrics Syst. Pharmacol. (2015)4, Aug. 1, 2015, pp. 481-488.

Harpaz, Rave et al., "Mining multi-item drug adverse effect associations in spontaneous reporting systems", BMC Bioinformatics, Oct. 28, 2010;11 Suppl 9:S7. doi: 10.1186/1471-2105-11-S9-S7, 8 pages.

High, Rob, "The Era of Cognitive Systems: An Inside Look at IBM Watson and How it Works", IBM Corporation, Redbooks, Dec. 12, 2012, 16 pages.

Xiang, Yang et al., "Efficiently mining Adverse Event Reporting System for multiple drug interactions", AMIA Summits on Translational Science Proceedings, Apr. 7-11, 2014, pp. 120-125.

Yuan, Michael J., "Watson and healthcare, How natural language processing and semantic search could revolutionize clinical decision support", IBM Corporation, IBM developerWorks, http://www.IBM.com/developerworks/industry/library/ind-watson/, Apr. 12, 2011, 14 pages.

Bazila, Banu A. et al., "A Novel Approach for Detecting Rare Drug-Drug Interaction Using Data Mining", Advances in Natural and Applied Sciences, 8.16: 75(9), Sep. 2014, 12 pages.

Harpaz, Rave et al., "Performance of Pharmacovigilance Signal Detection Algorithms for the FDA Adverse Event Reporting System", Clin Pharmacol Ther. Jun. 2013, 93(6), Clin Pharmacol Ther., Author Manuscript; Available in PMC Jun. 1, 2014, 19 pages.

Hauben, Manfred et al., "The Role of Data Mining in Pharmacovigilance", Expert Opinion on Drug Safety, 4:5, Sep. 2005, 21 pages.

Heba, I. et al., "Novel Data-Mining Methodologies for Detecting Drug-Drug Interactions: A Review of Pharmacovigilance Literature", Advances in Environmental Sciences, Development and Chemistry, Jun. 2014, 15 pages.

Lorberdaum, Tal, "Discovering New Drug-Drug Interactions Using Data Science: Applications to Drug-Induced Long QT Syndrome", Submitted in partial fulfillment of the requirements for the degree of Doctor of Philosophy under the Executive Committee of the Graduate School of Arts and Science, Columbia University, Aug. 2017, 157 pages.

Tatonetti, Nicholas P. et al., "A Novel Signal Detection Algorithm for Identifying Hidden Drug-Drug Interactions in Adverse Event Reports", Journal of the American Medical Informatics Association 2012;19, Published Online First Jun. 14, 2011, pp. 79-85.

Wang, Xiaoyan et al., "Active Computerized Pharmacovigilance Using Natural Language Processing, Statistics, and Electronic Health Records: A Feasibility Study", Journal of the American Medical Informatics Association, vol. 16, No. 3, May/Jun. 2009, pp. 328-337.

International Search Report and Written Opinion dated May 29, 2019 for International Application No. PCT/IB2019/051186, 9 pages.

* cited by examiner

| | DRUG PATTERN (E.G., ABC, AB, ETC.) | CONTAIN THE ADRS | DO NOT CONTAIN THE ADRS |
|---|---|---|---|
| 210 | CONTAINS ALL DRUGS IN THE PATTERN | A | B |
| 220 | DO NOT CONTAIN ANY DRUG IN THE PATTERN | C | D |

FINDING PRECISE CAUSAL MULTI-DRUG-DRUG INTERACTIONS FOR ADVERSE DRUG REACTION ANALYSIS

This application is a continuation of application Ser. No. 15/913,221, filed Mar. 6, 2018, status pending.

BACKGROUND

The present application relates generally to an improved data processing apparatus and method and more specifically to mechanisms for finding precise casual multi-drug-drug interactions for adverse drug reaction analysis.

An adverse drug reaction (ADR) is an injury caused by taking a medication or drug. ADRs may occur following a single dose or prolonged administration of a drug. ADRs may be classified by severity and cause. ADRs may be local or systemic. The study of ADRs is the concern of the field known as pharmacovigilance.

Causality assessment is used to determine the likelihood that a drug caused a suspected ADR. There are a number of different methods used to judge causation, including the Naranjo algorithm, the Venulet algorithm, and the World Health Organization (WHO) causality term assessment criteria. Each have pros and cons associated with their use and most require some level of expert judgment to apply. However, assigning causality to a specific agent often proves difficult, unless the event is found during a clinical study or large databases are used. Both methods have difficulties and can be fraught with error. Even in clinical studies, some ADRs may be missed as large numbers of test individuals are required to find the ADR.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a framework for learning multiple drug-adverse drug reaction associations. The method comprises receiving, by the framework, real world evidence comprising patient electronic medical record data and adverse drug reaction data and analyzing, by a co-occurrence logic module of the framework, the real world evidence to identify co-occurrences of references to drugs with references to adverse drug reactions (ADRs) to thereby generate candidate rules specifying multiple drug-ADR relationships. The method further comprises filtering, by a confounder filter logic module of the framework, the candidate rules to remove a subset of one or more rules having confounder drugs specified in the subset of one or more candidate rules, and thereby generate a filtered set of candidate rules. Moreover, the method comprises generating, by a causal association logic module of the framework, a causal model based on the filtered set of candidate rules, wherein the causal model comprises, for each ADR in a set of ADRs, a corresponding set of one or more rules, each rule specifying a combination of drugs having a causal relationship with the ADR.

In some illustrative embodiments, analyzing the real world evidence includes identifying all co-occurrences of references to drugs with references to ADRs in the real world evidence and generating the candidate rules based on the identified co-occurrences, where each candidate rule specifies a drug pattern identifying a plurality of drugs, and a corresponding ADR. Moreover, in some illustrative embodiments, analyzing the real world evidence further includes selecting a sub-set of the candidate rules as a basis for generating the candidate multiple drug-ADR relationships based on at least one of a support metric and a confidence metric, where the support metric measures a number of instances of the co-occurrence, corresponding to the candidate rule, in the real world evidence, and where the confidence metric measures, for a candidate rule, a probability of the ADR given the drugs in the drug pattern of the candidate rule.

In some illustrative embodiments, identifying all co-occurrences of references to drugs with reference to ADRs in the real world evidence includes performing natural language processing of the real world evidence to identify at least one of terms, phrases, or medical codes identifying references to drugs and references to ADRs, evaluating relative distances within the real world evidence, between each identified term, phrase or medical code identifying references to drugs and references to ADRs, and identifying co-occurrences based on the relative distances.

In some illustrative embodiments, selecting a sub-set of candidate rules includes, for each candidate rule, generating a contingency table data structure, where each entry in the contingency table data structure comprises a number of patient electronic medical records, that satisfy a condition of the row and column of the contingency table data structure corresponding to the entry. In the contingency table data structure, a first row of the contingency table data structure corresponds to patient electronic medical records that contain all drugs in the drug pattern of the candidate rule, a second row of the contingency table data structure corresponds to patient electronic medical records that contain none of the drugs in the drug pattern of the candidate rule, a first column of the contingency table data structure corresponds to the patient electronic medical records that contain the ADR in the candidate rule, and a second column of the contingency table data structure corresponds to the patient electronic medical records that do not contain the ADR in the candidate rule.

In still other illustrative embodiments, each candidate rule specifies a corresponding drug pattern and corresponding adverse drug reaction, and filtering the candidate rules further includes calculating, for each first candidate rule, an improvement metric specifying an amount of improvement of a corresponding association score for the first candidate rule over an association score for another second candidate rule specifying a sub-pattern of the corresponding drug pattern of the first candidate rule, and the corresponding adverse drug reaction of the first candidate rule. Moreover, filtering the candidate rules may further include determining, for each first candidate rule, whether to maintain the first candidate rule or remove the first candidate rule based on a value of the improvement metric.

In some illustrative embodiments, determining, for each first candidate rule, whether to maintain the candidate rule or remove the candidate rule based on a value of the improvement metric includes comparing the improvement metric corresponding to the first candidate rule to an improvement metric threshold value, and in response to the improvement metric corresponding to the first candidate rule not being equal to or greater than the improvement metric threshold value, determining that a confounder drug is present in the corresponding first drug pattern. Moreover, in some illustrative embodiments, determining, for each first candidate rule, whether to maintain the first candidate rule or remove the first candidate rule based on the value of the improvement metric further includes identifying the confounder drug in the corresponding drug pattern based on a difference between the corresponding drug pattern and the sub-pattern.

In other illustrative embodiments, the method further includes evaluating other patient electronic medical record data by applying the causal model to drug history data present in the other patient electronic medical record data to identify probabilities of a patient encountering one or more ADRs in the set of ADRs. Moreover, in some illustrative embodiments, the method also includes generating, for the patient, a patient model based on the identified probabilities of the patient encountering one or more ADRs in the set of ADRs. Furthermore, in some illustrative embodiments, the method comprises inputting the patient model into a cognitive system which implements the patient model to perform a cognitive operation based on the patient model. In some illustrative embodiments, the cognitive operation is a treatment recommendation operation that provides a treatment recommendation to a medical practitioner based on an evaluation of the other patient electronic medical record data by the cognitive system, and the patient model.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
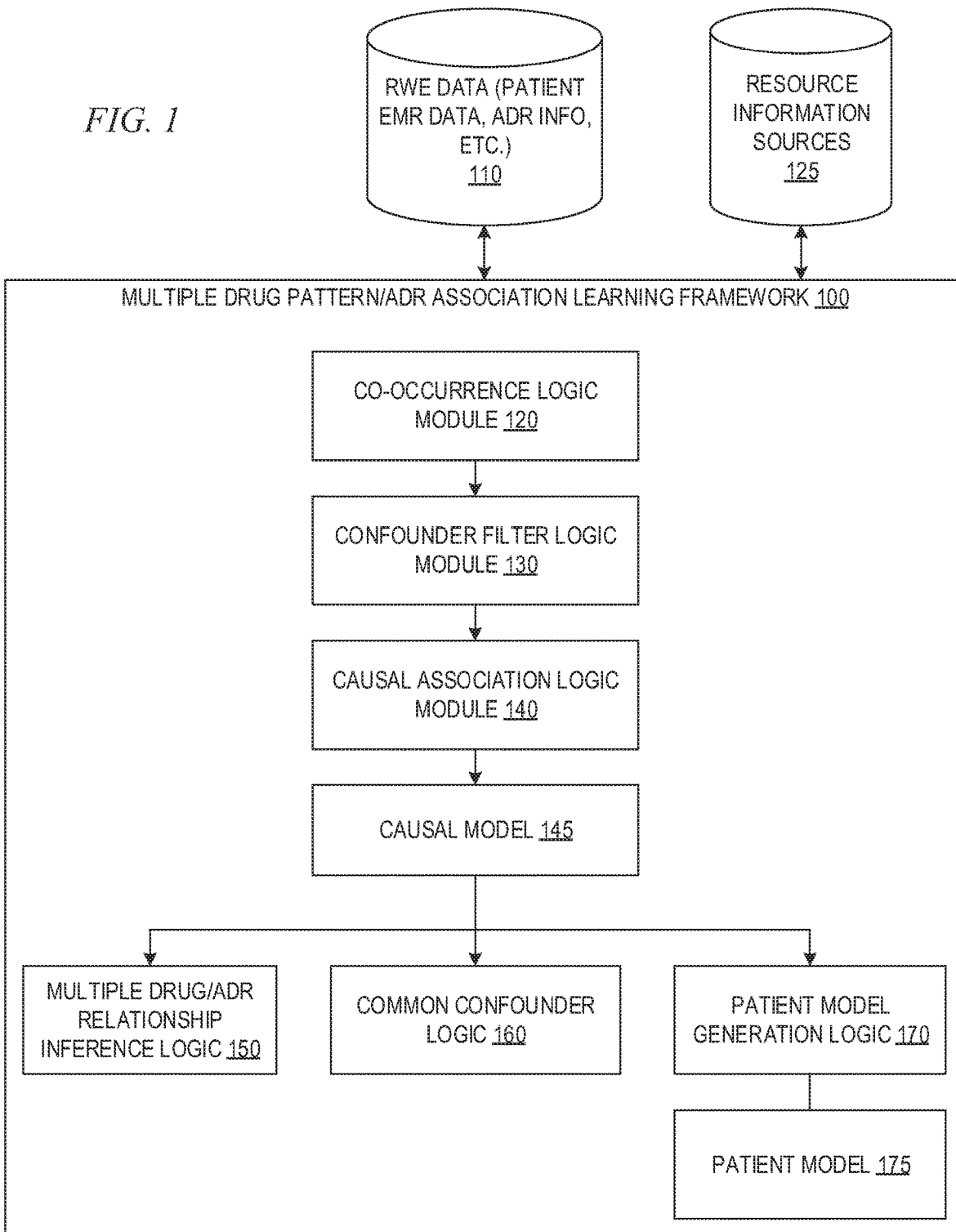
FIG. 1 is an example flow diagram illustrating an overall representation of the methodology employed by the mechanisms of one illustrative embodiment.

The strengths of current cognitive systems, such as current medical diagnosis, patient health management, patient treatment recommendation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is the ability to learn and take into consideration drug-drug interactions and determining causality with regard to adverse drug reactions (ADRs) when patients are taking multiple drugs.

That is, patients often take multiple drugs contemporaneously. This may be due to the patient having multiple different conditions for which different drugs are being taken to address each of the conditions, may be due to a treatment regimen requiring multiple drugs for treatment of a medical condition, or any of a number of other reasons. The patient's taking of multiple drugs may, or may not, be known by an individual medical practitioner when treating the patient. That is, if the patient is being treated by different medical practitioners for different medical conditions, one medical practitioner may not be aware of drugs prescribed by the other practitioner if that information is not present in the patient's local medical file and/or is not reported by the patient to the medical practitioner.

One of the key ways to treat various medical conditions, e.g., diseases such as diabetes, cancer, etc., is to place the patient on a treatment regimen that requires the administering of multiple medications, drugs, supplements, or the like (referred to collectively herein as "drugs"). For example, in treating Diabetes Type II, a first line treatment is typically a single drug while a second line treatment may comprise multiple drugs, e.g., metformin and another drug that may depend on the particular patient condition. Even though precautions are taken to avoid negative interactions of drugs, medical personnel are not always aware of all of the possible negative interactions. Moreover, there may be interactions based on the patient's particular attributes and comorbidities that make using treatments involving multiple drugs an issue, which may not be readily apparent to the medical personnel. Furthermore, patients often have more than one medical condition, e.g., chronic diseases, and may be on different drugs for the different medical conditions, leading to additional potential for negative interactions of drugs.

Drug-Drug interactions are serious threats that can result in significant morbidity and mortality, causing nearly 74,000 emergency room visits and 195,000 hospitalizations each year in the United States of America. The illustrative embodiments set forth herein provide mechanisms to identify causal multiple drug-drug interactions responsive for adverse drug reactions (ADRs) from real world evidence. The illustrative embodiments utilize an association rule mining approach for effectively identifying higher dimensional or higher order drug-drug associations from observational data. Statistical scores are used to identify the precise drug-drug interactions to filter out confounders. Furthermore, obtained rules (both higher-order and singleton drugs) related to a particular ADR are input into a Bayesian framework for building a causal discovery framework. The illustrative embodiments interpret the obtained parameters of the Bayesian framework for causal discovery. This causal discovery may be used by cognitive systems to assist medical personnel in evaluating and treating patients by providing additional information regarding the causal relationships between drugs being taken by patients and their potential for causing adverse drug reactions whether alone or in combination with other drugs that the patient may be taking. Moreover, the causal discovery assists medical personnel in eliminating potential sources of ADRs as simply confounders, thereby avoiding erroneous diagnosis and/or erroneous evaluation of the causes of ADRs.

The illustrative embodiments provide significant advantages over previous approaches to finding ADRs associated with drugs. Previous approaches to finding ADRs associated with drugs mainly focus on finding simple co-occurrences of drugs with ADRs from observational data and spontaneous reporting systems. For example, Harpaz et al., "Mining Multi-Item Drug Adverse Effect Associations in Spontaneous Reporting Systems," BMC Bioinformatics, Oct. 28, 2010; 11(9):S7 describes an approach that applies a generic association rule mining framework for finding associations based on simple co-occurrences of drugs. As another example, Xiang et al., "Efficiently Mining Adverse Event Reporting System for Multiple Drug Interactions," AMIA Summits on Translational Science Proceedings, 2014; 2014: 120 describes a methodology that also uses an association rule mining framework for finding minimal representations of drug-drug interactions. In yet another example, Du et al., "Graphic Mining of High-Order Drug Interactions and Their Directional Effects on Myopathy Using Electronic Medical Records," CPT: Pharmacometrics & Systems Pharmacology, Aug. 1, 2015; 4(8):481-8 describes a statistical approach for finding drug interactions for myopathy.

The illustrative embodiments, on the other hand, provide mechanisms which exploit the higher order associations of the drug-drug interaction from electronic health records. Moreover, the mechanisms of the illustrative embodiments remove the drugs, from the multi-drug associations, that are simple confounders that are co-prescribed for co-morbidities. In addition, the mechanisms of the illustrative embodiments may be used to predict ADRs (one or more) that are associated with multi-drug associations of particular patients as may be identified by a cognitive analysis of the patients' electronic medical records (EMRs).

The mechanisms of the illustrative embodiments operate based on the observation that ADRs may be caused by interactions among multiple drugs rather than caused by a single drug. The known approaches noted above have limitations in that they cannot find causal higher-order, i.e. higher dimension, interactions among multiple drugs and do not provide a generally applicable approach to finding such higher order multiple drug-drug interactions with corresponding ADRs. The term "higher order" as used herein refers to having two or more drugs as the casual factor to lead to one or more ADRs, which is denoted by a rule, e.g., $D_1D_2 \rightarrow ADR_1$ or $D_1D_2D_3 \rightarrow ADR_1ADR_2$, where $D_x$ is a drug and $ADR_y$ is an adverse drug reaction, and $\rightarrow$ represents a causal relationship of the rule. The prior art approaches based on simple co-occurrences of drugs with ADRs do not necessarily provide a causal relationship due to the prior art approaches finding only simple co-occurrences of a drug with an ADR and not being able to identify actual causal relationships. Moreover, such prior art approaches cannot differentiate drugs that have actual causal relationships from drugs that are simply co-prescribed due to a co-morbidity of the patient. Such co-prescribed drugs can act as mere confounders rather than a causal factor of ADRs. The illustrative embodiments provide mechanisms that determine actual causal relationships of multiple drugs with ADRs, eliminating confounders.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general-purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As discussed above, finding multi-drug-drug interactions responsible for ADRs using observational data is useful for finding real world evidence. Moreover, it has been determined that some drugs in multi-drug situations can be a simple confounder prescribed together with other drugs for comorbidities rather than real causal interactions with other drugs. A confounder drug is an extraneous drug that, in a statistical model, correlates (directly or inversely) with both the dependent drug variable and the independent drug variable in the model. Thus, some drugs may not actually contribute to particular ADRs and may not have an actual causal interaction with the ADRs.

The illustrative embodiments described herein leverage data mining algorithms, such as association rule mining with Bayesian models, for example, for finding the real causal interaction among multiple drugs with the ADRs from real world evidence data. In so doing, the illustrative embodiments identify multi-drug interactions responsible for ADRs as well as the confounders. Thus, the illustrative embodiments provide a computerized solution to finding causal relationships between multiple drugs and ADRs present in patient EMR data, as well as computerized solutions for eliminating confounder drugs from such relationships. The mechanisms of the illustrative embodiments are specifically directed to a computerized tool that performs such operations and thereby causes a computing system to perform cognitive operations that approximate human thought processes with regard to evaluating patient EMR data and determining causal relationships between multiple drugs and ADRs. While this computing tool approximates this human thought process, it does so using operations that are only performed by computing devices specifically configured to perform the operations of the illustrative embodiments, which differ from the processes a human mind employs due to the nature of the computing environment.

The illustrative embodiments provide a general approach to finding higher-order associations for multiple drugs with ADRs that will be helpful for finding rare ADRs that are only caused by interactions among drugs, which can be leveraged to prescribe safe drugs for patients with comorbidities. The illustrative embodiments may also determine which drugs in a multi-drug combination are only confounders instead of contributing to an interaction and ADR. This will assist with target risk management strategies, for example a drug label change could specify which drugs to avoid in combination rather than withholding the drug from all patients who happen to take the confounding drug.

FIG. 1 is an example flow diagram illustrating an overall representation of the methodology employed by the mechanisms of one illustrative embodiment. The methodology employs three main computerized logic modules 120-140 which operate on real word evidence (RWE) which may comprise various types of data obtained from various different sources of information. For example, the RWE 110 may comprise patient electronic medical records (EMRs), health insurance claims data, medication history information (such as may be obtained from a pharmacy computing system, health insurance records, physician's computing system, and/or the like), etc.

The computerized logic modules 120-140 may be implemented in specially configured computer hardware, software executed on computer hardware which thereby causes the hardware to perform operations the hardware did not perform prior to being configured with the software for execution, or any combination of specialized configured computer hardware and software executed on computer hardware. It should be appreciated that the loading of software into a memory of the computing device or data processing system, with subsequent execution of this software by one or more processors of the computing device, data processing system, specifically configures the computing device or data processing system to implement the specific computerized solution provided by the illustrative embodiments of the present invention. The computerized solution is a solution for providing computer aided evaluation of patient electronic medical record data, adverse drug reaction data, and other resource data, to identify real causal relationships between multiple drugs and a corresponding adverse drug reaction, without erroneously including confounder drugs, which previously was not able to be performed. The problems with prior art solutions as discussed herein lie in the reliance on mere co-occurrence of a reference to a drug and a reference to an ADR as evidence of a causal relationship, which may not in fact actually exist. Thus, the hardware/software mechanisms of the illustrative embodiments provide a computer solution to a computer based problem.

As shown in FIG. 1, in one illustrative embodiment, the computerized logic modules 120-140 comprise co-occurrence logic module 120, confounder filter logic module 130, and causal association logic module 140. The co-occurrence logic module 120 operates on the RWE 110 and generates co-occurrence output data that is provided to the confounder filter logic module 130. The co-occurrence output data specifies the co-occurrences of drugs and ADRs found in the RWE 110. The confounder filter logic module 130 evaluates this co-occurrence output data to filter out instances of co-occurrences of drugs and ADRs which actually represent confounders and not potential causalities between those drugs and the ADRs. As discussed hereafter, this may be done using an improvement score mechanism for filtering such co-occurrences based on improvement score and one or more established thresholds. The output of the confounder filter logic module 130 is provided to the causal association logic module 140 which builds a causality model 145, such as a Bayesian network model or the like. The causality model 145 may be applied by various cognitive system logic 150-170 to identify interactions of multiple drugs with ADRs 150, identify common confounders 160, and predict ADRs for patients 170.

The logic modules 120-140 define a data mining framework 100 that identifies multi-drug interactions that are responsible for a set of ADRs. In general, these logic modules first perform association rule mining, identify and remove confounder drugs, and generate a causal model having causal rules between multiple drugs and corresponding ADRs or ADR groups based on the remaining association rule relationships having removed the confounder drugs. As shown in FIG. 1, the framework 100 utilizes the co-occurrence logic module 120 to process the RWE data 110 and identify all possible combinations of drugs and ADRs that occur more frequently in the RWE 110 data. "More frequently" may be evaluated based on a predetermined threshold or other predefined criteria set for identifying combinations of drugs and ADRs that should be considered as potential causal relationships. For example, one or more thresholds may be set using a technique based on two metrics of association analysis, where these two metrics are called support and confidence. The support metric, or support score, measures the number of instances of the co-occurrences, or a number of instances of the particular rule, i.e. both the drugs and ADRs are present, while the confidence metric, or confidence score, measures the probability of having the ADRs given the drugs. Thereafter, a threshold is applied to both of these metrics or scores, e.g., support scores equal to or above 70% and confidence scores equal to or above 85%, to get a set of rules as the "frequent" rules.

The co-occurrence logic module 120 may maintain a data structure to store these two metrics (Support and Confidence metrics) of each association rule associating a combination of two or more drugs with an ADR or ADR group. All possible combination of drugs and ADRs are searched systematically using this data structure for better computational efficiency, since it requires a combinatorial search over the drugs and ADRs as potential candidate of rules. More specifically, the co-occurrence logic module 120 may start with a simple rule with one drug and one ADR to obtain the two metrics for such rules, and then explore higher-order rules using this metrics data structure. An anti-monotonic property called a-priori rule is applied to filter out non-interesting higher-order rules from the data.

For example, drugs A, B, and C may be found in the RWE 110 data, which again may comprise patient medication history information in association with identifications of ADRs, in patient EMR data, for example, where the patient EMR data may be EMR data for a plurality of patients. Hence, various instances of combinations of drugs A, B, and C may be also identified as being associated with the identification of an ADR, e.g., the adverse drug reaction P in the depicted example case. For example, there may be indications that a combination of A and B are associated with the ADR in the content of the patient EMR. Moreover, there may be indications that a combination of A and C are also associated with the ADR, as well as A, B, and C in the patient EMR.

The co-occurrence logic module 120 may utilize various resource information sources 125 to perform natural language processing of structured and unstructured (e.g., natural language document) data to identify key terms, phrases, medical codes, and the like, that are indicative of particular drugs and adverse drug reactions. The resource information sources 125 may comprise various types of resource information that can be used as a basis for identifying portions of content in the RWE 110 data that correspond to drugs and adverse reactions. For example, the resource information may include natural language medical journal data, medical guidelines document data, drug label data, known adverse drug reaction (ADR) data associated with drug data, drug interaction data, and the like. As an example, information regarding drug-drug interactions are often found in natural language documentation such as clinical statements, guidelines, and in some patient statements. Drug-drug interaction information may also be provided by drug manufacturers, health organizations, governmental organizations, and other sources in various forms. One example of a source of drug information that includes drug-drug interaction information, is the Gold Standard Drug Database, available from Elsevier. Moreover, domain specific dictionaries of terms and phrases, medical code reference documents, and the like, may be used to specify identifiable terms, phrases, and medical codes that may be identified in content of the RWE 110 data.

The co-occurrence logic module 120 may analyze the relative distance (e.g., in the same entry, within a certain number of words, within a certain number of entries, etc.) between instances of identifiers of drugs and instances of terms/phrases/medical codes, etc. indicative of an ADR to determine associations, e.g., if the drug instance in the patient EMR is present within a same encounter entry as the indicator of the ADR, then there may be an association. Moreover, the co-occurrence logic module 120 may also look to temporal information present in the RWE 110 data to determine whether there is a co-occurrence of an instance of a drug with an instance of another drug and with an ADR. For example, if the patient is prescribed a drug and an instance of an ADR is recorded within a specified time period after the prescribing of the drug, then a co-occurrence may be determined to exist. Similarly, such temporal determinations may be made with regard to prescribing multiple drugs. Moreover, the duration of time over which the patient is supposed to be taking the drugs that they are prescribed may be evaluated to determine if more than one drug is likely being taken by the patient at approximately the same time, and approximately the same time as a reported ADR. In addition, natural language processing may be performed on entries in the patient EMR data to identify terms/phrases indicative of associations, such as terms like "caused" or "results in", or the like. Various distance based, temporal based, and/or natural language processing-based evaluations of the RWE 110 data may be performed by the co-occurrence logic module 120, using the resource information from the resource information sources, to identify co-occurrences of drugs with other drugs and with ADRs.

Another source of information for finding drug-ADR associations is the publicly available post-marketing surveillance data obtained from several drug monitoring organizations, such as the Food and Drug Administration (FDA) and Side Effect Resource (SIDER). In particular, these types of post-marketing data are created based on the reported ADRs of a certain drug from patients or medical providers after the patient has been using the drug for a certain period of time. Such case reports are well-validated and documented by the FDA. Similarly, another source of such publicly available dataset can be the SIDER dataset, which is crafted from side-effects reported in the drug labels using Current Procedural Terminology (CPT) codes.

The evaluations of these various factors for identifying co-occurrences of drugs with other drugs and with ADRs may be used to calculate association scores for various combinations and associations of drugs and ADRs. That is, the co-occurrence logic module 120 may calculate, for each combination of drugs determined to have co-occurrence in the RWE 110, an association score representing a strength of the association between that particular combination or pattern or drugs and the co-occurring ADR found in the RWE 110. Put another way, the co-occurrences may be represented as candidate rules specifying a drug pattern identifying a plurality of drugs, which have a candidate causal relationship with an ADR. Thus, for a candidate rule ABC→P, for example, corresponding to a co-occurrence of a drug pattern ABC and an adverse drug reaction P, the association score represents the probability or likelihood that P will occur given ABC, i.e. how strong the association is between the drug pattern and the ADR. It should be noted that the association score corresponding to an association of a set of drugs (e.g., ABC, AB, AC, BC, and so on) with one or more ADRs (e.g., P or any higher order combination of ADRs containing P), can be generated using any statistical tests or measures, such as the support metrics and confidence metrics mentioned above and/or other metrics or scores, such as Chi-square, mutual-information, or any other suitable statistical test or measure.

Figures 2, 4:
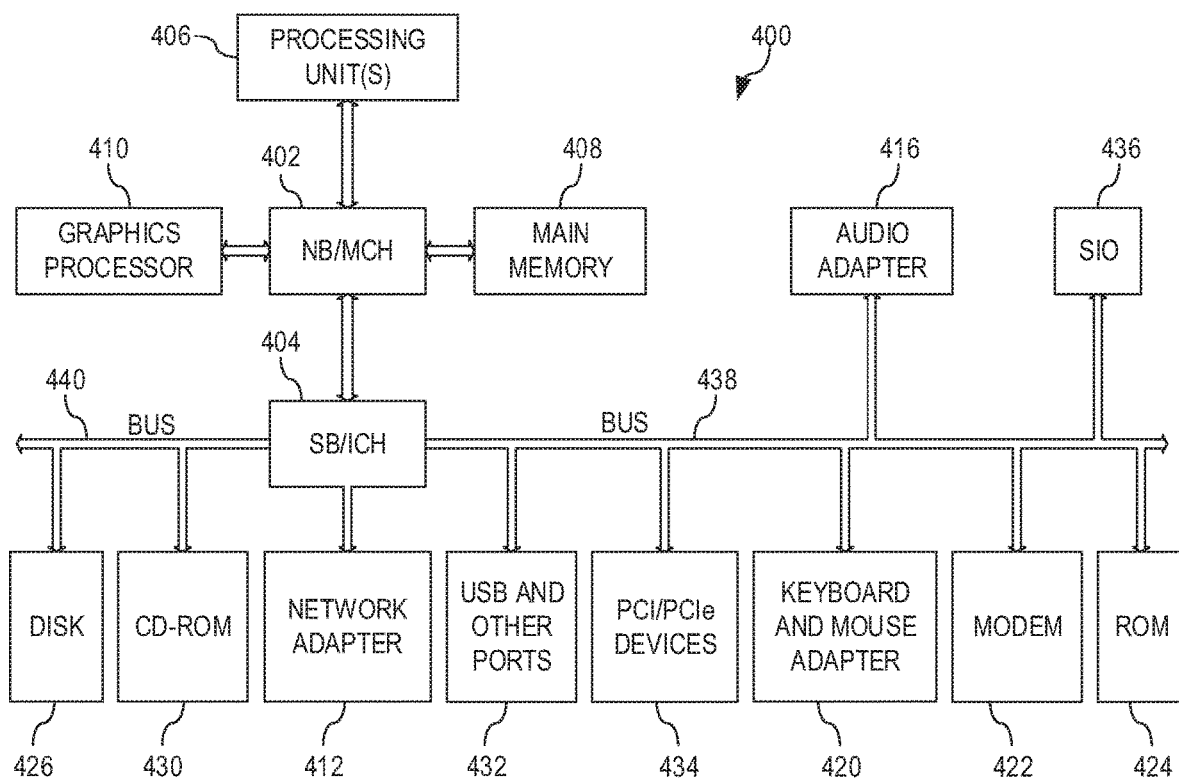
FIG. 2 is an example diagram of a contingency table in accordance with one illustrative embodiment.
FIG. 4 is an example block diagram of a data processing system in which aspects of the present invention may be implemented in accordance with one illustrative embodiment.

All these statistical tests or measures can be computed based on a contingency table, such as the contingency table shown in FIG. 2, for example. In statistics, a contingency table is a type of table in a matrix format that displays the (multivariate) frequency distribution of the variables. Contingency tables provide a basic picture of the interrelation between two variables and can help find interactions between them.

As shown in FIG. 2, each entry in the contingency table 200 denotes the number of case reports, e.g., patients or patient EMRs, from the RWE 110 data that satisfies the conditions of the rows and columns of the contingency table 200, e.g., each case, or patient EMR, that has either the complete drug pattern (row 210) or none of the drugs in the complete drug pattern (row 220), and which is either associated with the ADR (column 230) or not associated with the ADR (column 240) in the case or patient EMR. A contingency table 200 may be generated for each drug pattern, e.g., ABC, and sub-drug pattern, e.g., AB, AC, and BC, and a corresponding evaluation based on the contingency table 200 for each drug pattern and sub-drug pattern may be performed by the co-occurrence logic module 120.

In the example depicted in FIG. 2, only 'AND' logic is considered and not 'OR' logic throughout. Thus, a pattern, or rule, containing drugs "ABC" means A 'AND' B 'AND' C. Therefore, if a case, e.g. patient EMR, includes only some of the drugs, then the case does not contain the rule. For example, a patient case containing drugs ABDE is satisfying the rule (AB→P), but not (ABC→P).

By evaluating the various associations, it can be determined that not all co-occurrences of drugs A, B, and C with the ADR of P represent real interactions among the drugs A, B and C. Rather, they can represent confounders due to co-prescribed drugs due to comorbidities of patients. Thus, there is a need to find the difference of the higher order combination ABC and each of its sub-drug combinations, AB, AC, and BC. If the lower-order drug combinations and the higher order drug combinations have similar or higher association score, e.g., an association score based on the defined metrics, such as support and confidence metrics, than the higher order drug combinations associated with an ADR, then confounder drugs may be identified and removed so as to identify the real multi-drug correlations with ADRs. For example, if AC has a relatively high association score but ABC has a relatively lower association score, then the drug C may be considered a confounder. On the other hand, if these sub-drug combinations have association scores that are relatively low, and the association scores of the higher-level drug combinations are relatively higher, then real higher-order interactions can be identified.

In particular, the confounder filter logic module 130 may implement logic that generates a newly designed metric, referred to as "Improvement", which may be evaluated by the confounder filter logic module 130 for a particular combination of drugs to measure their association with ADRs that is beyond the association of any of its subsets of drugs with the same ADRs. In the case of an example of drug pattern ABC and its association with an adverse drug reaction P, i.e. ABC→P, the Improvement score may be denoted as follows:

$$Imp(ABC \rightarrow P) = Score(ABC \rightarrow P) - \max_{(\alpha \in ABC)} Score(\alpha \rightarrow P)$$

where Imp is the Improvement metric for the association of the drug pattern with an ADR, i.e. ABC with P in this example, and Score is the association score of the drug pattern with the ADR, which can be the support, confidence, Chi-square, mutual information, etc. This equation checks how much the Score improved in this higher order pattern (ABC→P) from any of its sub-patterns, as denoted by α. From all such sub-patterns a, the max Scores are considered of all such α's. This Improvement score will be very low if any of drugs in the drug pattern is a simple confounder (e.g., if C is always co-prescribed with the drug A and B, then the score (ABC→P) will be the same as the score (AB→P)). On the other hand, the Improvement score will be higher for the true interactions among drugs and ADRs, and thus it will be able to filter out true interactions among multiple drugs with ADRs from the simple confounders.

The confounder filter logic module 130 calculates, for each of the drug patterns, the Improvement score and compares the Improvement scores to a threshold Improvement score value. If the Improvement score is equal to or above the threshold Improvement score value, then it is determined that there are no confounders in the drug pattern. If the Improvement score is below the threshold Improvement score value, then it is determined that the drug pattern contains a confounder and the confounder is identified using the sub-drug patterns associated with the drug pattern. For example, if it is found that Imp(ABC→P) is low and Imp(AB→P) is high, then C is a confounder and the real drug-drug interaction that has a causal relationship with the ADR of P is AB→P.

Having filtered out any confounder drugs in the drug patterns based on the evaluation of the Improvement scores, the remaining drug patterns are operated on by the causal association logic module 140 to infer a causal model 145 on all of the remaining drug patterns for a certain ADR group to enhance the interpretability of the model. The ADR group may be a single ADR or a plurality of ADRs categorized into a same ADR group based on similar characteristics. The ADR group may be defined a priori, such as based on medical resource information 125, subject matter expert configuration of the framework 100, or the like. For example, the subject matter expert configuration of the framework 100 may include predefined relationships among ADR terms. Such relationships among ADRs can be defined based on their common symptoms or other medical ontologies defined by different terms, such as ICD-9 codes.

For example, in accordance with one illustrative embodiment, all drug patterns, including sub-drug patterns, remaining after the operation of the confounder filter logic module 130 to filter out drug patterns having confounder drugs, are summarized in a Bayesian learning framework using a directed acyclic graph. Basically, a Bayesian network is inferred for each ADR or ADR group of interest from the potential causal rules involving that ADR or ADR group based on the operation of the confounder filter logic module 130. Note that, the singleton rules can easily be represented in a directed acyclic graph (DAG), however the higher order patterns consisting of multiple drugs require some modifications so that they can also be represented by a DAG. Without loss of generalizability, the illustrative embodiments represent all such patterns containing multiple drugs into a new dummy variable. For example, a rule of ABC→P is represented by $\beta_1$→P, where $\beta_1$ represents the interaction among the three drugs A, B and C. Here, the new dummy variable is considered as a binary variable along with other singleton patterns which contain the same ADR or ADR groups. Once, all such patterns are represented in a DAG, the transition probabilities among the variables are learned, which provides the final causal model 145.

Based on the causal model 145, multiple drug/ADR relationship inference logic 150 may be implemented to infer the causal relationships among multiple drugs that are responsible for a particular ADR or ADR group. In particular, the rules may be extracted from the Bayesian network for each ADR under consideration as the final set of rules containing drugs and ADRs. Also, the confounders obtained from the confounder filter logic module 130 can also be output as common confounders to the common confounders logic module 160 which may output such common confounder information and/or perform other processing of the common confounders, such as updating or generating additional resource information to improve resource information sources 125 to specifically identify the common confounders, or the like. The inferred causal relationships and confounders may be used to improve the interpretability among the relationships among the drugs and ADRs. This knowledge can further be used during clinical decision making by physicians and other medical personnel treating patients by identifying real multiple drug interaction relationships with ADRs and identifying confounder drugs to the clinical decision makers.

It should be noted that the inferred causal relationships may be utilized by a cognitive system, such as a cognitive decision support system for assisting medical practitioners in treating patients, as an information source for assisting with the cognitive operations performed by the cognitive system. For example, if a treatment is being evaluated for a patient, and the treatment comprises one or more drugs that have a causal relationship with an ADR as determined through the mechanisms of the illustrative embodiments, an evaluation may further be made as to whether the patient is also prescribed or taking another drug in a drug pattern that has a causal relationship with the ADR. If so, the cognitive system may modify rankings or scores associated with such treatments to reflect the lower preference for selecting that treatment and may provide information in association with an output of the treatment recommendation indicating the causal relationship between the drug, in combination with one or more other drugs, and the ADR.

In some cases, the causal relationship information may be used as a basis for outputting a notification to medical personnel, drug providers, governmental organizations, or the like, to inform them of the identified causal relationships between the drug patterns and corresponding ADRs. For example, such notifications may be used as a way to update drug label information, medical reference documents, government guideline documents, or the like. The notification may specify the drug patterns and the associated ADRs, as well as a basis for indicating the association between the drug patterns and the ADRs, e.g., the association scores, the Improvement scores, and any confounder drugs identified through the operation of the present invention.

Moreover, the identification of confounders by the confounder filter logic 130 may be used by common confounder identification logic 160 to identify common confounders for particular ADRs and/or ADR groups. This information may be used for notification purposes and/or may be used by a cognitive system to assist with identifying confounder drugs prescribed to patients, as discussed hereafter.

In some illustrative embodiments, a patient model 175 can be generated by patient model generation logic 170, based on the results of the determinations that identify the causal relationships between drug patterns and an ADR, as well as the removal of confounders. This patient model 175 may then be used to predict ADRs for other patients based on the drug history information for these other patients, which can be leveraged for clinical decision making. In particular, the Bayesian model generated by the causal association logic module 140 as the causal model 145 can be used to find the ADRs with highest probability for the patient's drug history by comparing the rules in the causal model 145 to the drug history of the patient's specific EMR data, i.e. finding the drugs specified in the drug history of the patient EMR data that match drugs specified in the rules of the causal model 145 with which an ADR is associated and providing a corresponding notification to indicate a probability of an ADR being associated with the patient. This patient model 175 may be provided to, or integrated into, a cognitive system which may assist with such clinical decision making by predicting, for a particular patient, based on their drug history information in their patient EMR data, whether the patient is likely to experience the ADRs associated with the drugs that the patient is taking.

From the above description, it should be apparent that the illustrative embodiments may be utilized in many different types of data processing environments. In order to provide a context for the description of the specific elements and functionality of the illustrative embodiments, FIGS. 3-6 are provided hereafter as example environments in which aspects of the illustrative embodiments may be implemented. It should be appreciated that FIGS. 3-6 are only examples and are not intended to assert or imply any limitation with regard to the environments in which aspects or embodiments of the present invention may be implemented. Many modifications to the depicted environments may be made without departing from the spirit and scope of the present invention.

FIGS. 3-6 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for generating treatment recommendations for patients or cognitive evaluation of a patient's EMR data for various decision support operations, based on a cognitive evaluation of their medical condition(s), patient attributes, available candidate treatments as indicated in one or more corpora of medical documentation, and the like. In particular, with specific importance to the present application, drug-drug interaction information and association with adverse drug reactions (ADRs) is learned and applied during evaluation of candidate treatments for the patient so as to select and present treatment recommendations that take into consideration the drug-drug interactions of the various treatments as well as with other drugs the patient may be taking for other medical conditions.

In some embodiments, the healthcare cognitive system may be employed to simply review a patient's EMR data to identify potential or predicted ADRs based on the drug history information in the patient's EMR data and the learned associations of drug patterns with ADRs or ADR groups as described previously. Notifications may output to medical practitioners comprising the identification of the ADR predictions, the reasons for such ADR predictions, confounder drugs identified, and/or other information about the applicable drug patterns and associated ADRs so as to assist them with treating the patient for their medical conditions. In still other illustrative embodiments, such notifications of associations of drug patterns with ADRs or ADR groups may be automatically generated and output to appropriate drug providers, industry or governmental oversight organizations, or the like, so as to inform them of the identified drug pattern associations with ADRs and thereby provide them with information that may be used to update drug labels, medical reference documentation, governmental or industry guidelines, and the like.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What treatment applies to patient P?", the cognitive system may instead receive a request of "generate a treatment for patient P," or the like. As another example, a question may be of the type "What adverse drug reactions is the patient likely to have?", while a request may be of the type "Identify adverse drug reactions for this patient." It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing treatment recommendations for patients that take into consideration drug-to-drug interactions when evaluating the efficacy of the treatment for a particular patient and the particular patient's attributes, medical condition(s), other drugs being taken for treatment of the same or other medical conditions, and the like. In taking into account the drug-drug interactions, the mechanisms of the illustrative embodiments may learn and identify drug patterns that are associated with adverse drug reactions (ADRs), and then may apply the learned associations, which may be defined in terms of a causal model generated by the mechanisms of the illustrative embodiments, or a patient model as discussed above, to the prediction of potential ADRs for a patient, the evaluation of a candidate treatment based on the learned multiple drug pattern and ADR associations with the patient's own personal medical conditions, attributes, and treatments, such as may be determined from patient electronic medical records (EMRs), or the like. The prediction or evaluation of ADRs based on the drug history of a patient may be used to modify the ranking or confidence values associated with candidate treatments, indicating a confidence that the candidate treatment is a viable treatment for the particular patient, e.g., if there is a likelihood of an ADR, then the confidence may be reduced. The resulting ranked listing of candidate treatments may then be used to select one or more treatment recommendations to be output to a medical practitioner to assist the medical practitioner is treating the patient. Moreover, notifications of the predicted ADRs may be output to the medical practitioners and/or appropriate oversight organizations.

As some of the illustrative embodiments may be implemented in, or in conjunction with, a healthcare cognitive system, it is beneficial to understand how such cognitive systems, and question and answer creation in a cognitive system implementing a QA pipeline, is implemented. It should be appreciated that the mechanisms described in FIGS. 3-6 are only examples and are not intended to state or imply any limitation with regard to the type of cognitive system mechanisms with which the illustrative embodiments are implemented. Many modifications to the example cognitive system shown in FIGS. 3-6 may be implemented in various embodiments of the present invention without departing from the spirit and scope of the present invention.

Moreover, some illustrative embodiments of the present invention may be implemented independent of any cognitive system. That is, the mechanisms described previously with regard to FIGS. 1 and 2 may be implemented as a separate entity which operates to learn associations of drug patterns with ADRs for purposes of notification and generation of models that may assist medical practitioners and/or providers or drugs to avoid such ADRs in patients. In other words, while some illustrative embodiments may integrate the framework 100 of the illustrative embodiments into the operation of a cognitive system, other embodiments may not include the cognitive system or require the cognitive system. Hence, again, FIGS. 3-6 are only examples of possible implementations of illustrative embodiments and are not intended to be limiting on the possible implementations or embodiments.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information usable by the QA pipeline to identify these question and answer attributes of the content. The annotated content may be processed to generate an in-memory representation of the documents in the corpus/corpora. This process is sometimes referred to as ingestion of the documents or the corpus/corpora, which may result in an indexed set of documents with metadata specifying features of the documents.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

Figure 3:
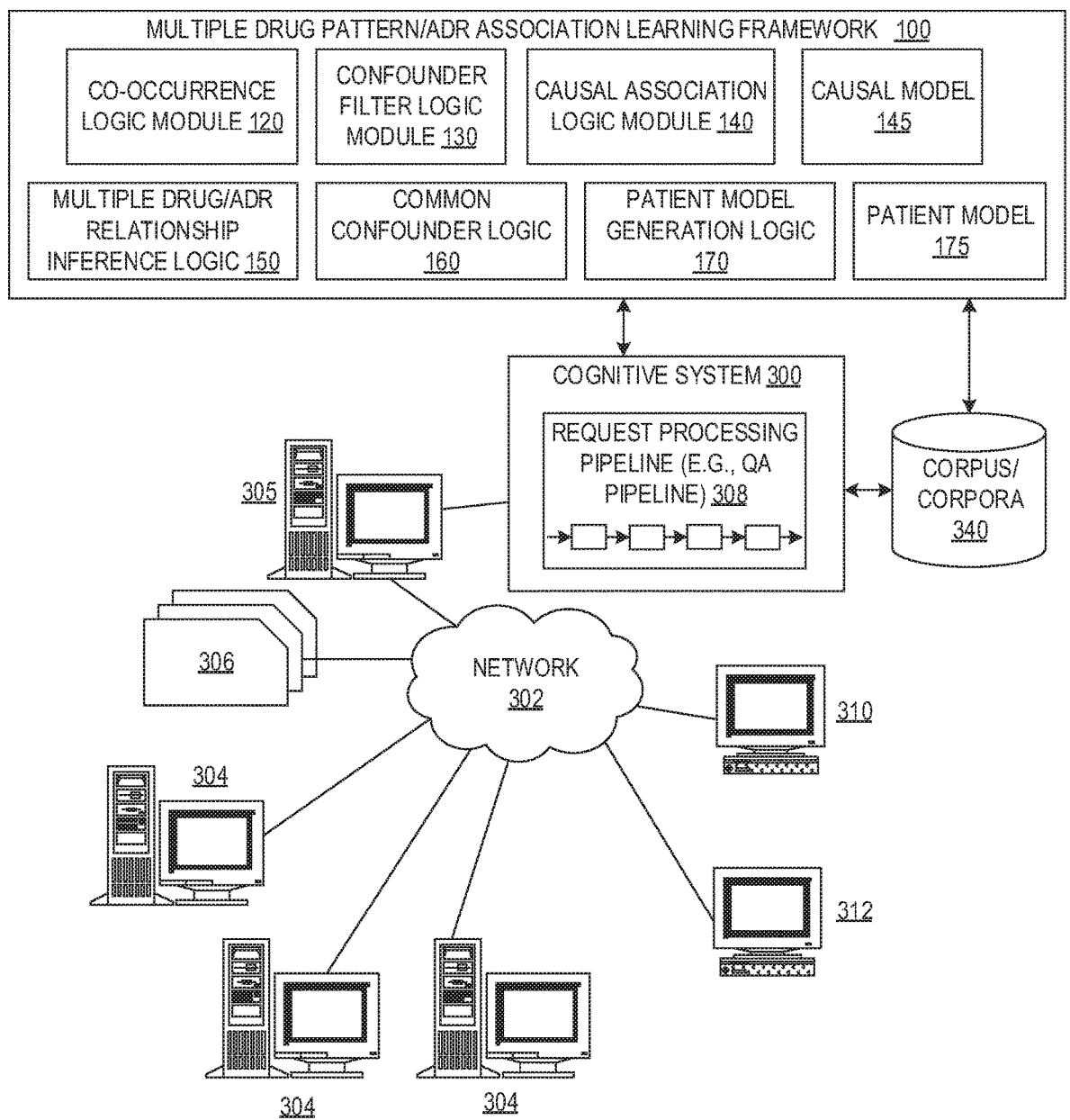
FIG. 3 is an example diagram of a distributed data processing system environment in which aspects of one illustrative embodiment may be implemented.

FIG. 3 depicts a schematic diagram of one illustrative embodiment of a cognitive system 300 implementing a request processing pipeline 308, which in some embodiments may be a question answering (QA) pipeline, in a computer network 302. For purposes of the present description, it will be assumed that the request processing pipeline 308 is implemented as a QA pipeline that operates on structured and/or unstructured requests in the form of input questions.

The cognitive system 300 is implemented on server computing device 305, which may comprise one or more computing devices comprising one or more processors and one or more memories, and potentially any other computing device elements generally known in the art including buses, storage devices, communication interfaces, and the like. The server computing device 305 is connected to the computer network 302. For purposes of illustration only, FIG. 3 depicts the cognitive system 100 being implemented on computing device 305 only, but in some illustrative embodiments, the cognitive system 300 may be distributed across multiple computing devices, such as one or more of a plurality of computing devices 304 and 305.

The network 302 includes multiple computing devices 304 and 305, which may operate as server computing devices, and 310-312 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 300 and network 302 enables question processing and answer generation (QA) functionality for one or more cognitive system users via their respective computing devices 310-312. In other embodiments, the cognitive system 300 and network 302 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 300 may be used with components, systems, subsystems, and/or devices other than those that are depicted herein.

The cognitive system 300 is configured to implement a request processing pipeline 308 that receive inputs from various sources. The requests may be posed in the form of a natural language question, natural language request for information, natural language request for the performance of a cognitive operation, or the like. For example, the cognitive system 300 receives input from the network 302, a corpus or corpora of electronic documents 306, 340, cognitive system users, and/or other data and other possible sources of input. In one embodiment, some or all of the inputs to the cognitive system 300 are routed through the network 302. The various computing devices 304, 305, 310, 312 on the network 302 include access points for content creators and cognitive system users. Some of the computing devices 304, 305 include devices for a database storing the corpus or corpora of data 306, 340. Portions of the corpus or corpora of data 306, 340 may also be provided on one or more other network attached storage devices, in one or more databases, or other computing devices not explicitly shown in FIG. 3. The network 302 includes local network connections and remote connections in various embodiments, such that the cognitive system 300 may operate in environments of any size, including local and global, e.g., the Internet.

In one embodiment, the content creator creates content in a document of the corpus or corpora of data 306, 340 for use as part of a corpus of data with the cognitive system 300. The document includes any file, text, article, or source of data for use in the cognitive system 300. Cognitive system users access the cognitive system 300 via a network connection or an Internet connection to the network 302, and input questions/requests to the cognitive system 300 that are answered/processed based on the content in the corpus or corpora of data 106, 340. In one embodiment, the questions/requests are formed using natural language. The cognitive system 300 parses and interprets the question/request via a pipeline 308, and provides a response to the cognitive system user, e.g., cognitive system user 310, containing one or more answers to the question posed, response to the request, results of processing the request, or the like. In some embodiments, the cognitive system 300 provides a response to users in a ranked list of candidate answers/responses while in other illustrative embodiments, the cognitive system 300 provides a single final answer/response or a combination of a final answer/response and ranked listing of other candidate answers/responses.

The cognitive system 300 implements the pipeline 308 which comprises a plurality of stages for processing an input question/request based on information obtained from the corpus or corpora of data 306, 340. The pipeline 308 generates answers/responses for the input question or request based on the processing of the input question/request and the corpus or corpora of data 306. The pipeline 308 will be described in greater detail hereafter with regard to FIG. 6.

In some illustrative embodiments, the cognitive system 300 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 306, 340. Based on the application of the queries to the corpus or corpora of data 306, 340, a set of hypotheses, or candidate answers/responses to the input question/request, are generated by looking across the corpus or corpora of data 306, 340 for portions of the corpus or corpora of data 306, 340 that have some potential for containing a valuable response to the input question/response (hereafter assumed to be an input question). The pipeline 308 of the IBM Watson™ cognitive system then performs deep analysis on the language of the input question and the language used in each of the portions of the corpus 306, 340 found during the application of the queries using a variety of reasoning algorithms.

The scores obtained from the various reasoning algorithms are then weighted against a statistical model that summarizes a level of confidence that the pipeline 108 of the IBM Watson™ cognitive system 300, in this example, has regarding the evidence that the potential candidate answer is inferred by the question. This process is repeated for each of the candidate answers to generate a ranked listing of candidate answers which may then be presented to the user that submitted the input question, e.g., a user of client computing device 310, or from which a final answer is selected and presented to the user. More information about the pipeline 308 of the IBM Watson™ cognitive system 300 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 300 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, drug-drug interaction information and adverse drug reaction information in patient electronic medical records (EMRs) and/or in natural language documents, and the like, to provide a healthcare oriented cognitive system result.

In the context of the present invention, cognitive system 300 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 300 may be a healthcare cognitive system 300 that operates in the medical or healthcare type domains and which may process requests for such healthcare operations via the request processing pipeline 308 input as either structured or unstructured requests, natural language input questions, or the like. In some illustrative embodiments, the cognitive system 300 is a cognitive healthcare system that provides medical treatment recommendations for patients and their medical condition(s) based on a variety of factors which includes, among other factors, drug-to-drug interactions as learned and applied by the mechanisms of one or more of the illustrative embodiments described herein.

As shown in FIG. 3, the cognitive system 300 is further augmented, in accordance with the mechanisms of the illustrative embodiments, to include logic implemented in specialized hardware, software executed on hardware, or any combination of specialized hardware and software executed on hardware, for implementing a multiple drug pattern/adverse drug reaction (ADR) association learning framework 100, which in this depicted embodiment includes the co-occurrence logic module 120, the confounder filter logic module 130, causal association logic module 140, causal model 145, multiple drug/ADR relationship inference logic 150, common confounder logic 160, patient model generation logic 170, and patient model 175. The RWE data 110 and resource information sources 125 shown in FIG. 1 may be part of one or more of the corpora 306, 340 shown in FIG. 3 and may be accessed by the framework 100 via one or more network based connections and/or local connections as needed. It should be appreciated that the framework 100 and the components 120-175 of the framework 100 operate in the manner previously described above with regard to FIGS. 1 and 2.

With regard to the interaction of the framework 100 with the cognitive system 300, this interaction may take many different forms depending upon the desired implementation and particular illustrative embodiment. As noted above, the framework 100 provides identification of associations of multiple drug patterns with ADRs by inferring such relationships from the causal model built by identifying co-occurrences of drug patterns and ADRs, such as by module 120, filtering out of confounder drugs, such as by module 130, and generating a causal model 145, such as by way of module 140. This causal model 145 is evaluated to infer relationships between multiple drug patterns and ADRs or ADR groups, such as by logic 150. Moreover, common confounder drugs for ADRs or ADR groups are identified, such as by logic 160. Furthermore, a patient model 175 may be generated, such as by patient model generation logic 170, which may be used by a cognitive system 300 to predict the likelihood of a patient experiencing an ADR, based on the learned and inferred multiple drug pattern/ADR relationships.

The multiple drug pattern/ADR relationships, common confounder drugs for ADRs or ADR groups, and the patient model may be provided as information sources to the cognitive system 300 which is modified to operate on such information when performing cognitive operations, as previously discussed above. For example, such information may be evaluated by the request processing pipeline 308 of the cognitive system 300 when evaluating candidate treatments for a patient, evaluating a patient's EMR data in general, evaluating a patient for candidacy for a medical trial, generating notifications to medical practitioners regarding identified drug/ADR relationships, sending notifications to drug providers and/or oversight organizations regarding identified drug/ADR relationships, and the like.

The framework 100 learns, through a machine learning process, the drug-drug interactions, or multiple drug patterns, that are associated with particular ADRs or ADR groups and which drugs are confounders in such patterns. In some illustrative embodiments, the framework 100 may further comprise logic that may be used to further evaluate the specific information for a patient, such as the drugs being taken by a patient for the medical condition(s) of the patient, candidate treatments and their corresponding drugs which are being considered for treating a patient, as determined by the cognitive system, and the like. The evaluation may provide an output indicating the ADRs that the patient may be predicted to experience based on the drug information associated with the patient, the candidate treatments, etc. Moreover, the framework 100 may provide indications of confounder drugs associated with the patient information, the candidate treatments, etc. This information may be provided back to the cognitive system for use in performing cognitive operations, such as for use in generating confidence scores associated with candidate treatments, ranking of candidate treatments, providing notifications, and the like.

It should be appreciated that the various components of the framework 100 show in the figures may be provided as software instructions stored in memory and executed by one or more processors of one or more data processing systems that are specifically configured to implement the framework 100, which may be one or more of the processors provided by the server computing device 105, or distributed over a plurality of computing devices, such as server 105 and one or more of the servers 104. Alternatively, some of the logic provided by the components of the framework 100 may be embodied in hardware devices, firmware, or the like. Moreover, while the components of the framework 100 are shown in the figures as example components to illustrate the operation of the illustrative embodiments, it should be appreciated that the framework 100 may comprise additional logic that is not specifically shown in the figures but which may support and assist with the functionality of the components 120-175. Unless otherwise indicated herein, operations or functions described as being performed by the framework 100 that are not specifically attributed to one of the components 120-175 may be performed by this other logic provided in the framework 100 that is not specifically shown, e.g., controller logic, interface logic, storage logic, and/or the like.

Moreover, while the framework 100 is shown as a separate entity from the cognitive system 300 in FIG. 3 for ease of depiction, it should be appreciated that one or more of the components 120-175 may be integrated in and/or utilize logic and resources of the cognitive system 300 to perform their operations. For example, the framework 100 may make use of the natural language processing (NLP) and annotator mechanisms of the cognitive system 300 to perform operations for parsing and identifying drug-drug interaction, or drug pattern, and ADR association information in natural language documents. Moreover, the patient model 175 may be integrated with or operate in conjunction with scoring and ranking logic of the cognitive system 300 for scoring and ranking candidate answers, or candidate treatments, in order to select one or more candidate treatments to output as treatment recommendations.

As noted above with regard to FIGS. 1 and 2, the illustrative embodiments provide mechanisms for learning relationships or associations of multiple drug patterns with ADRs or ADR groups and confounder drugs in such multiple drug patterns. This machine learning of relationships of multiple drug patterns with ADRs and confounder drugs may be used to build predictive models that can be used to predict whether a particular patient is likely to experience an ADR. Moreover, in some implementations, these models may be used to predict whether candidate treatments for a patient will likely result in an ADR and thereby modify the applicability of the candidate treatment to the patient or at least generate a notification of the potential of the ADR for consideration by medical practitioners when treating the patient. In still other illustrative embodiments, such machine learning of relationships may be used to send notifications to medical practitioners, drug providers and/or manufacturers, and industry/governmental oversight organizations, to inform them of learned associations or relationships between multiple drug patterns and ADRs or ADR groups, as well as confounder drugs.

The illustrative embodiments may modify the relative scoring and ranking of candidate treatments for the particular patient based on the determined drug-drug interactions and ADRs associated with the candidate treatments. Furthermore, the illustrative embodiments may output treatment recommendations with information indicating the reasons for the relative rankings of candidate treatments based on drug-drug interactions and associations with ADRs.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 4 is provided as an example of one type of data processing system in which aspects of the present invention may be implemented. Many other types of data processing systems may be likewise configured to specifically implement the mechanisms of the illustrative embodiments.

FIG. 4 is a block diagram of an example data processing system in which aspects of the illustrative embodiments are implemented. Data processing system 400 is an example of a computer, such as server 305 or client 310 in FIG. 3, in which computer usable code or instructions implementing the processes for illustrative embodiments of the present invention are located. In one illustrative embodiment, FIG. 4 represents a server computing device, such as a server 305, which implements a cognitive system 300 and request processing pipeline 308 augmented to include the additional mechanisms of the illustrative embodiments described herein. Alternatively, the server computing device 305 may be specifically configured to implement only the framework 100, as previously discussed above, which may operate on its own or in conjunction with a separate cognitive system, such as cognitive system 300.

In the depicted example, data processing system 400 employs a hub architecture including North Bridge and Memory Controller Hub (NB/MCH) 402 and South Bridge and Input/Output (I/O) Controller Hub (SB/ICH) 404. Processing unit 406, main memory 408, and graphics processor 410 are connected to NB/MCH 402. Graphics processor 410 is connected to NB/MCH 402 through an accelerated graphics port (AGP).

In the depicted example, local area network (LAN) adapter 412 connects to SB/ICH 404. Audio adapter 416, keyboard and mouse adapter 420, modem 422, read only memory (ROM) 424, hard disk drive (HDD) 426, CD-ROM drive 430, universal serial bus (USB) ports and other communication ports 432, and PCI/PCIe devices 434 connect to SB/ICH 404 through bus 438 and bus 440. PCI/PCIe devices may include, for example, Ethernet adapters, add-in cards, and PC cards for notebook computers. PCI uses a card bus controller, while PCIe does not. ROM 424 may be, for example, a flash basic input/output system (BIOS).

HDD 426 and CD-ROM drive 430 connect to SB/ICH 404 through bus 440. HDD 426 and CD-ROM drive 430 may use, for example, an integrated drive electronics (IDE) or serial advanced technology attachment (SATA) interface. Super I/O (SIO) device 436 is connected to SB/ICH 404.

An operating system runs on processing unit 406. The operating system coordinates and provides control of various components within the data processing system 400 in FIG. 4. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 400.

As a server, data processing system 400 may be, for example, an IBM® eServer™ System p® computer system, running the Advanced Interactive Executive (AIX®) operating system or the LINUX® operating system. Data processing system 400 may be a symmetric multiprocessor (SMP) system including a plurality of processors in processing unit 406. Alternatively, a single processor system may be employed.

Instructions for the operating system, the object-oriented programming system, and applications or programs are located on storage devices, such as HDD 426, and are loaded into main memory 408 for execution by processing unit 406. The processes for illustrative embodiments of the present invention are performed by processing unit 406 using computer usable program code, which is located in a memory such as, for example, main memory 408, ROM 424, or in one or more peripheral devices 426 and 430, for example.

A bus system, such as bus 438 or bus 440 as shown in FIG. 4, is comprised of one or more buses. Of course, the bus system may be implemented using any type of communication fabric or architecture that provides for a transfer of data between different components or devices attached to the fabric or architecture. A communication unit, such as modem 422 or network adapter 412 of FIG. 4, includes one or more devices used to transmit and receive data. A memory may be, for example, main memory 408, ROM 424, or a cache such as found in NB/MCH 402 in FIG. 4.

Those of ordinary skill in the art will appreciate that the hardware depicted in FIGS. 3 and 4 may vary depending on the implementation. Other internal hardware or peripheral devices, such as flash memory, equivalent non-volatile memory, or optical disk drives and the like, may be used in addition to or in place of the hardware depicted in FIGS. 3 and 4. Also, the processes of the illustrative embodiments may be applied to a multiprocessor data processing system, other than the SMP system mentioned previously, without departing from the spirit and scope of the present invention.

Moreover, the data processing system 400 may take the form of any of a number of different data processing systems including client computing devices, server computing devices, a tablet computer, laptop computer, telephone or other communication device, a personal digital assistant (PDA), or the like. In some illustrative examples, data processing system 400 may be a portable computing device that is configured with flash memory to provide non-volatile memory for storing operating system files and/or user-generated data, for example. Essentially, data processing system 400 may be any known or later developed data processing system without architectural limitation.

Figure 5:
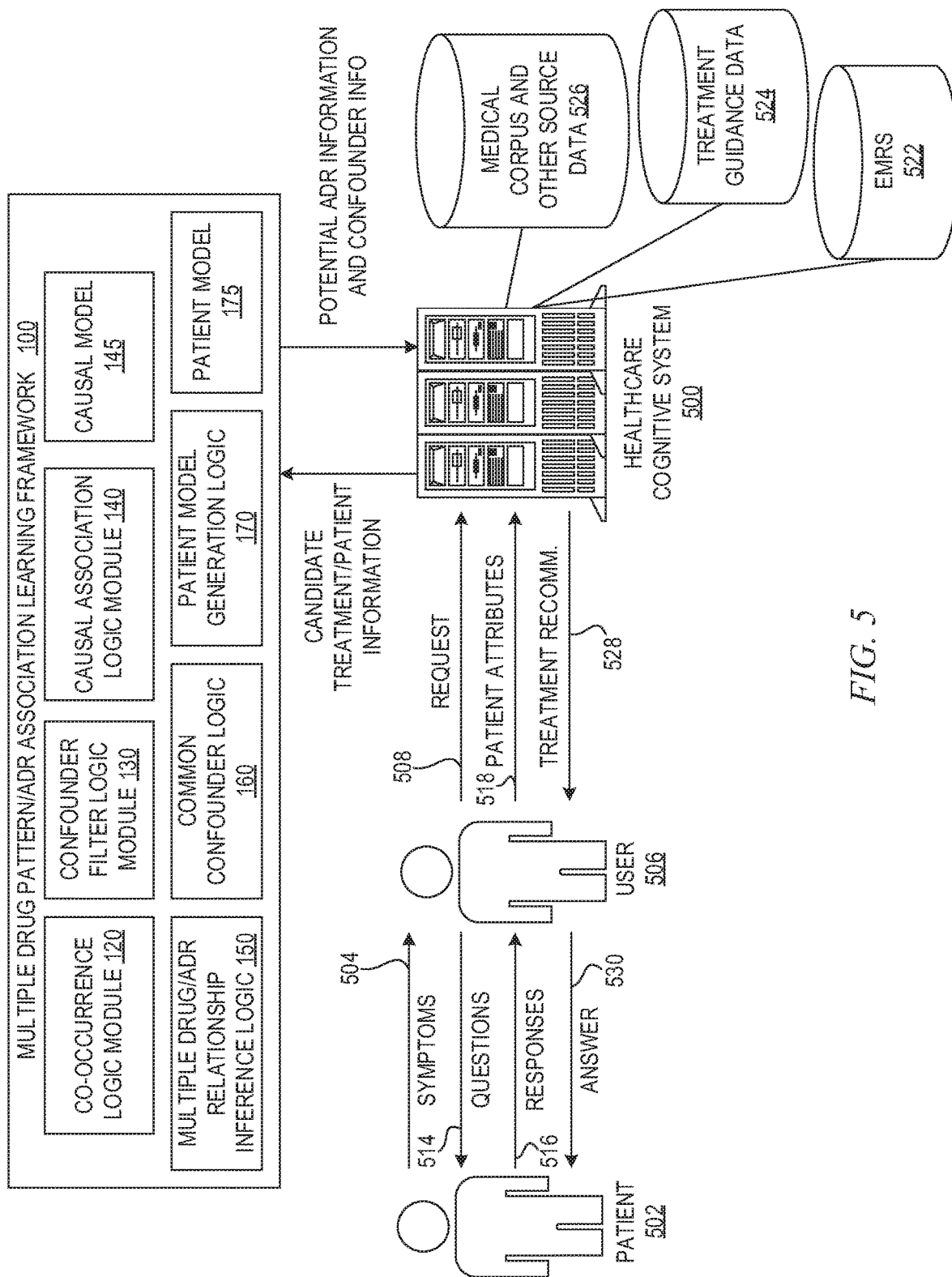
FIG. 5 illustrates an interaction of a multiple drug pattern/ADR association learning framework with a cognitive healthcare system in accordance with one illustrative embodiment.

FIG. 5 is an example diagram illustrating an interaction of elements of a healthcare cognitive system in accordance with one illustrative embodiment. The example diagram of FIG. 5 depicts an implementation of a healthcare cognitive system 500 that is configured to provide medical treatment recommendations for patients. However, it should be appreciated that this is only an example implementation and other healthcare operations may be implemented in other embodiments of the healthcare cognitive system 500 without departing from the spirit and scope of the present invention.

Moreover, it should be appreciated that while FIG. 5 depicts the patient 502 and user 506 as human figures, the interactions with and between these entities may be performed using computing devices, medical equipment, and/or the like, such that entities 502 and 506 may in fact be computing devices, e.g., client computing devices. For example, the interactions 504, 514, 516, and 530 between the patient 502 and the user 506 may be performed orally, e.g., a doctor interviewing a patient, and may involve the use of one or more medical instruments, monitoring devices, or the like, to collect information that may be input to the healthcare cognitive system 500 as patient attributes 518. Interactions between the user 506 and the healthcare cognitive system 500 will be electronic via a user computing device (not shown), such as a client computing device 310 or 312 in FIG. 3, communicating with the healthcare cognitive system 500 via one or more data communication links and potentially one or more data networks.

As shown in FIG. 5, in accordance with one illustrative embodiment, a patient 502 presents symptoms 504 of a medical condition to a user 506, such as a medical practitioner, technician, or the like. The user 506 may interact with the patient 502 via a question 514 and response 516 exchange where the user gathers more information about the patient 502, the symptoms 504, and the medical condition of the patient 502. It should be appreciated that the questions/responses may in fact also represent the user 506 gathering information from the patient 502 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 502. In some cases, such medical equipment may be medical equipment typically used in hospitals or medical centers to monitor vital signs and medical conditions of patients that are present in hospital beds for observation or medical treatment.

In response, the user 502 submits a request 508 to the healthcare cognitive system 500, such as via a user interface on a client computing device that is configured to allow users to submit requests to the healthcare cognitive system 500 in a format that the healthcare cognitive system 500 can parse and process. The request 508 may include, or be accompanied with, information identifying patient attributes 518, the medical condition diagnosed by the user 506, or the like. These patient attributes 518 may include, for example, an identifier of the patient 502 from which patient EMRs 522 for the patient may be retrieved, demographic information about the patient, the symptoms 504, and other pertinent information obtained from the responses 516 to the questions 514 or information obtained from medical equipment used to monitor or gather data about the condition of the patient 502. Any information about the patient 502 that may be relevant to a cognitive evaluation of the patient by the healthcare cognitive system 500 may be included in the request 508 and/or patient attributes 518.

The healthcare cognitive system 500 provides a cognitive system that is specifically configured to perform an implementation specific healthcare oriented cognitive operation. In the depicted example, this healthcare oriented cognitive operation is directed to providing a treatment recommendation 528 to the user 506 to assist the user 506 in treating the patient 502 based on their reported symptoms 504, medical condition, and other information gathered about the patient 502 via the question 514 and response 516 process and/or medical equipment monitoring/data gathering. The healthcare cognitive system 500 operates on the request 508 and patient attributes 518 utilizing information gathered from the medical corpus and other source data 526, treatment guidance data 524, and the patient EMRs 522 associated with the patient 502 to generate one or more treatment recommendation 528. The treatment recommendations 528 may be presented in a ranked ordering with associated supporting evidence, obtained from the patient attributes 518 and data sources 522-526, indicating the reasoning as to why the treatment recommendation 528 is being provided and why it is ranked in the manner that it is ranked.

For example, based on the request 508 and the patient attributes 518, the healthcare cognitive system 500 may operate on the request, such as by using a QA pipeline type processing as described herein, to parse the request 508 and patient attributes 518 to determine what is being requested and the criteria upon which the request is to be generated as identified by the patient attributes 518, and may perform various operations for generating queries that are sent to the data sources 522-526 to retrieve data, generate candidate treatment recommendations (or answers to the input question), and score these candidate treatment recommendations based on supporting evidence found in the data sources 522-526. In the depicted example, the patient EMRs 522 is a patient information repository that collects patient data from a variety of sources, e.g., hospitals, laboratories, physicians' offices, health insurance companies, pharmacies, etc. The patient EMRs 522 store various information about individual patients, such as patient 502, in a manner (structured, unstructured, or a mix of structured and unstructured formats) that the information may be retrieved and processed by the healthcare cognitive system 500. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 502, the patient's corresponding EMRs 522 from this patient repository may be retrieved by the healthcare cognitive system 500 and searched/processed to generate treatment recommendations 528.

The treatment guidance data 524 provides a knowledge base of medical knowledge that is used to identify potential treatments for a patient based on the patient's attributes 518 and historical information presented in the patient's EMRs 522. This treatment guidance data 524 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 524 may be provided in any suitable form that may be ingested by the healthcare cognitive system 500 including both structured and unstructured formats.

In some cases, such treatment guidance data 524 may be provided in the form of rules that indicate the criteria required to be present, and/or required not to be present, for the corresponding treatment to be applicable to a particular patient for treating a particular symptom or medical malady/condition. For example, the treatment guidance data 524 may comprise a treatment recommendation rule that indicates that for a treatment of Decitabine, strict criteria for the use of such a treatment is that the patient 502 is less than or equal to 60 years of age, has acute myeloid leukemia (AML), and no evidence of cardiac disease. Thus, for a patient 502 that is 59 years of age, has AML, and does not have any evidence in their patient attributes 518 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 502, then the treatment of Decitabine is a candidate treatment for consideration for this patient 502. However, if the patient had been 69 years old, the first criterion would not have been met and the Decitabine treatment would not be a candidate treatment for consideration for this patient 502. Various potential treatment recommendations may be evaluated by the healthcare cognitive system 500 based on ingested treatment guidance data 524 to identify subsets of candidate treatments for further consideration by the healthcare cognitive system 500 by scoring such candidate treatments based on evidential data obtained from the patient EMRs 522 and medical corpus and other source data 526.

For example, data mining processes may be employed to mine the data in sources 522 and 526 to identify evidential data supporting and/or refuting the applicability of the candidate treatments to the particular patient 502 as characterized by the patient's patient attributes 518 and EMRs 522. For example, for each of the criteria of the treatment rule, the results of the data mining provide a set of evidence that supports giving the treatment in the cases where the criterion is "MET" and in cases where the criterion is "NOT MET." The healthcare cognitive system 500 processes the evidence in accordance with various cognitive logic algorithms to generate a confidence score for each candidate treatment recommendation indicating a confidence that the corresponding candidate treatment recommendation is valid for the patient 502. The candidate treatment recommendations may then be ranked according to their confidence scores and presented to the user 506 as a ranked listing of treatment recommendations 528. In some cases, only a highest ranked, or final answer, is returned as the treatment recommendation 528. The treatment recommendation 528 may be presented to the user 506 in a manner that the underlying evidence evaluated by the healthcare cognitive system 500 may be accessible, such as via a drilldown interface, so that the user 506 may identify the reasons why the treatment recommendation 528 is being provided by the healthcare cognitive system 500.

One example of a healthcare cognitive system 500 which may be implemented and modified to incorporate the operations of the cognitive treatment recommendation system 540 of one or more of the illustrative embodiments, is described in co-pending and commonly assigned U.S. patent application Ser. No. 15/262,311, filed Sep. 12, 2016 and entitled "Medical Condition Independent Engine for Medical Treatment Recommendation System," which is hereby incorporated by reference. It should be appreciated that this is only one example of a cognitive healthcare system with which the mechanisms of the illustrative embodiments may be utilized. The mechanisms of the illustrative embodiments may be implemented with any cognitive healthcare system that evaluates patient EMR data and candidate treatment data to generate a treatment recommendation for treating the patient.

In accordance with the illustrative embodiments herein, the healthcare cognitive system 500 is augmented to include, or operate in conjunction with, the multiple drug pattern/ADR association learning framework 100 which operates in the manner described previously, with regard to the similar system 100 in FIG. 1 and one or more of the illustrative embodiments described above. The depiction in FIG. 5 is showing runtime operation of the cognitive treatment recommendation system 500 for assisting with the evaluation of candidate treatments for a particular patient. As such, it is assumed that the framework has already performed its initial operations for ingesting a corpus/corpus of information to generate causal model data structures, confounder information data structures, and the like, such as previously described above.

During runtime operation, the healthcare cognitive system 500 generates candidate treatments for the patient and provides this information along with patient information, e.g., patient EMR information including drug history information, to the framework 100. The framework 100, in the depicted example embodiment, may comprises logic that analyzes the candidate treatments to identify the drugs involved in the candidate treatments, identifies the drugs indicated as being actively administered to the patient for the same or different medical condition for which the candidate treatments are being considered, to thereby identify the drugs being taken by the patient and the drugs that are potentially going to be administered to the patient should the various candidate treatments be selected for treating the patient. The multiple drug patterns and associated ADRs or ADR groups associated with the identified drugs may be retrieved or accessed via the causal model 145, and indications of potential ADRs and confounder drugs may be generated for the candidate treatments. This information may be provided back to the healthcare cognitive system 500 for use in evaluating the confidence and/or ranking of the candidate treatments, such as by reducing the confidence scores and/or ranking of candidate treatments that are determined to have a probability of generating and adverse drug reaction (ADR).

As mentioned previously, in some illustrative embodiments, this treatment recommendation 528 may include a ranked listing of candidate treatments with corresponding explanations as to why certain candidate treatments are ranked lower based on drug-to-drug interactions. These explanations may indicate the specific drugs in the drug-drug interactions, i.e. the multiple drug patterns, that are causing a reduction in the ranking of the candidate treatment due to the probability of an ADR. The output of the treatment recommendation 528 may comprise a graphical user interface or other suitable notification mechanism.

While FIG. 5 is depicted with an interaction between the patient 502 and a user 506, which may be a healthcare practitioner such as a physician, nurse, physician's assistant, lab technician, or any other healthcare worker, for example, the illustrative embodiments do not require such. Rather, the patient 502 may interact directly with the healthcare cognitive system 500 without having to go through an interaction with the user 506 and the user 506 may interact with the healthcare cognitive system 500 without having to interact with the patient 502. For example, in the first case, the patient 502 may be requesting 508 treatment recommendations 528 from the healthcare cognitive system 500 directly based on the symptoms 504 provided by the patient 502 to the healthcare cognitive system 500. Moreover, the healthcare cognitive system 500 may actually have logic for automatically posing questions 514 to the patient 502 and receiving responses 516 from the patient 502 to assist with data collection for generating treatment recommendations 528. In the latter case, the user 506 may operate based on only information previously gathered and present in the patient EMR 522 by sending a request 508 along with patient attributes 518 and obtaining treatment recommendations in response from the healthcare cognitive system 500. Thus, the depiction in FIG. 5 is only an example and should not be interpreted as requiring the particular interactions depicted when many modifications may be made without departing from the spirit and scope of the present invention. It should be appreciated, however, that at no time should the treatment itself be administered to the patient 502 without prior approval of the healthcare professional treating the patient, i.e. final determinations as to treatments given to a patient will always fall on the healthcare or medical professional with the mechanisms of the illustrative embodiments serving only as an advisory tool for the healthcare or medical professional (user 506) and/or patient 502.

As mentioned above, the healthcare cognitive system 500 may include a request processing pipeline, such as request processing pipeline 308 in FIG. 3, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P." In some cases, the QA pipeline may receive an input question such as, "what ADRs is the patient likely to experience?" or a request, such as "tell me the ADRs the patient may experience."

Figure 6:
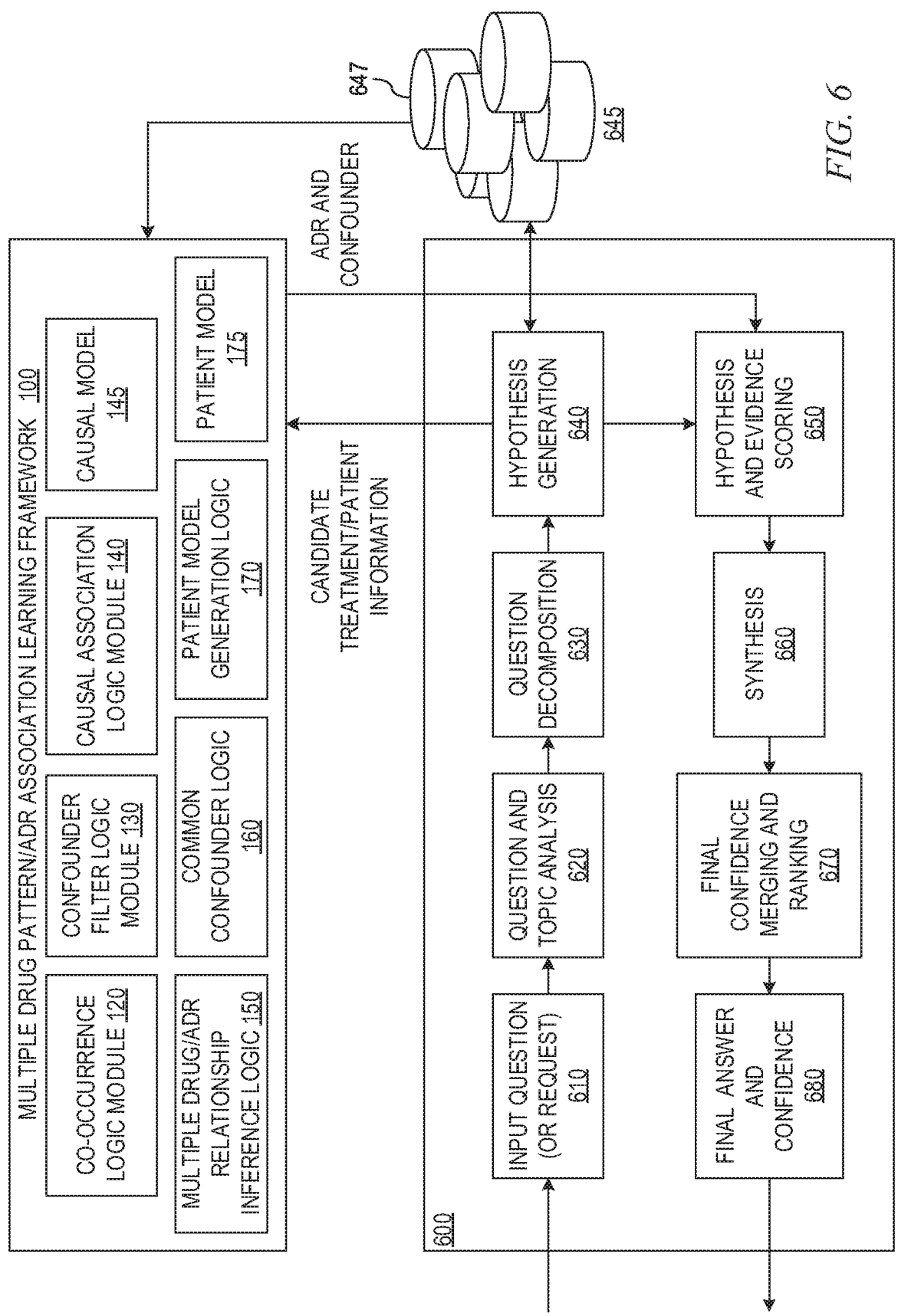
FIG. 6 illustrates an example of an interaction between a multiple drug pattern/ADR association learning framework with a question answering or request processing pipeline in accordance with one illustrative embodiment.

FIG. 6 illustrates a QA pipeline of a healthcare cognitive system, such as healthcare cognitive system 500 in FIG. 5, or an implementation of cognitive system 300 in FIG. 3, for processing an input question in accordance with one illustrative embodiment. It should be appreciated that the stages of the QA pipeline shown in FIG. 6 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 6 is augmented, for example, in one or more of the stages to implement the improved mechanism of the illustrative embodiments described hereafter, additional stages may be provided to implement the improved mechanism, or separate logic from the pipeline 600 may be provided for interfacing with the pipeline 600 and implementing the improved functionality and operations of the illustrative embodiments.

As shown in FIG. 6, the QA pipeline 600 comprises a plurality of stages 610-680 through which the cognitive system operates to analyze an input question and generate a final response. In an initial question input stage 610, the QA pipeline 600 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 600, i.e. the question and topic analysis stage 620, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 6, the identified major features are then used during the question decomposition stage 630 to decompose the question into one or more queries that are applied to the corpora of data/information 645 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 645. That is, these various sources themselves, different collections of sources, and the like, represent a different corpus 647 within the corpora 645. There may be different corpora 647 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 647 within the corpora 645.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 640 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 640, to generate hypotheses for answering the input question. These hypotheses are also referred to herein as "candidate answers" for the input question. For any input question, at this stage 640, there may be hundreds of hypotheses or candidate answers generated that may need to be evaluated.

The QA pipeline 600, in stage 650, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 660, the large number of scores generated by the various reasoning algorithms are synthesized into confidence scores or confidence measures for the various hypotheses. This process involves applying weights to the various scores, where the weights have been determined through training of the statistical model employed by the QA pipeline 600 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 600 that identifies a manner by which these scores may be combined to generate a confidence score or measure for the individual hypotheses or candidate answers. This confidence score or measure summarizes the level of confidence that the QA pipeline 600 has about the evidence that the candidate answer is inferred by the input question, i.e. that the candidate answer is the correct answer for the input question.

The resulting confidence scores or measures are processed by a final confidence merging and ranking stage 670 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 680, a final answer and confidence score, or final set of candidate answers and confidence scores, are generated and output to the submitter of the original input question via a graphical user interface or other mechanism for outputting information.

As shown in FIG. 6, in accordance with one illustrative embodiment, the framework 100 may ingest and learns multiple drug interactions or multiple drug patterns, and their associations with ADRs or ADR groups, as well as confounder drugs and the like, during an initial ingestion operation for ingesting portions of the corpora 645, which may include patient EMR data having drug history information, medical reference documents, etc. as previously discussed above. The framework 100 may generate a causal model 145 based on the processing of the components 120-140 and a patient model 175 based on the causal model and the operation of one or more of the components 150-170. These models may be used to identify such multiple drug pattern relationships with ADRs or ADR groups.

As shown in FIG. 6, the various candidate treatments generated as hypotheses in the hypothesis generation stage 640 of the pipeline 600 may be provided to the framework 100 which may comprise logic for applying the learned multiple drug pattern/ADR relationships or associations and confounder drug information to the candidate treatments and patient information to identify potential ADRs that the patient may experience. This may involve applying the patient model 175 and causal model 145 information to the specific combinations of drugs that the patient is taking and may take based on the candidate treatments. The framework 100 may then return any identified ADRs and confounder information for the candidate treatments back to the hypothesis and evidence scoring stage logic 650 of the pipeline which may utilize that information in generating confidence scores and rankings for the various candidate treatments. The remainder of the processing by the pipeline 600 may continue on as described above so as to generate one or more final candidate treatment answers.

Thus, the illustrative embodiments provide mechanisms for building a causal model that comprises rules that specify causal relationships between multiple drugs and corresponding adverse drug reactions (ADRs) or ADR groups. The building of this causal model comprises deep analysis of real world evidence (RWE), potentially based on various resource data structures providing knowledge for evaluating terms, phrases, codes, etc., indicative of relationships between drugs and ADRs. The building of the causal model comprises identifying co-occurrences of drugs with ADRs in the RWE, identifying confounder drugs in these co-occurrences, and filtering out the co-occurrences of drugs with ADRs that have such confounder drugs present. The causality model built may comprise the rules that do not have confounder drugs present such that each ADR or ADR group may have an associated set of one or more rules specifying causal relationships of two or more drugs with the ADR or ADR group. This causal model may then be applied to other patient data to determine a probability that the patient may encounter an ADR based on the drugs being taken by that patient. Such application of the causal model to specific patient data may be performed in conjunction with other cognitive operations being performed by a cognitive system as noted above. Thus, the operation of the cognitive system is improved by the implementation of the causal model generated by the illustrative embodiments which comprises actual real causal relationships with confounders having been removed.

Figure 7:
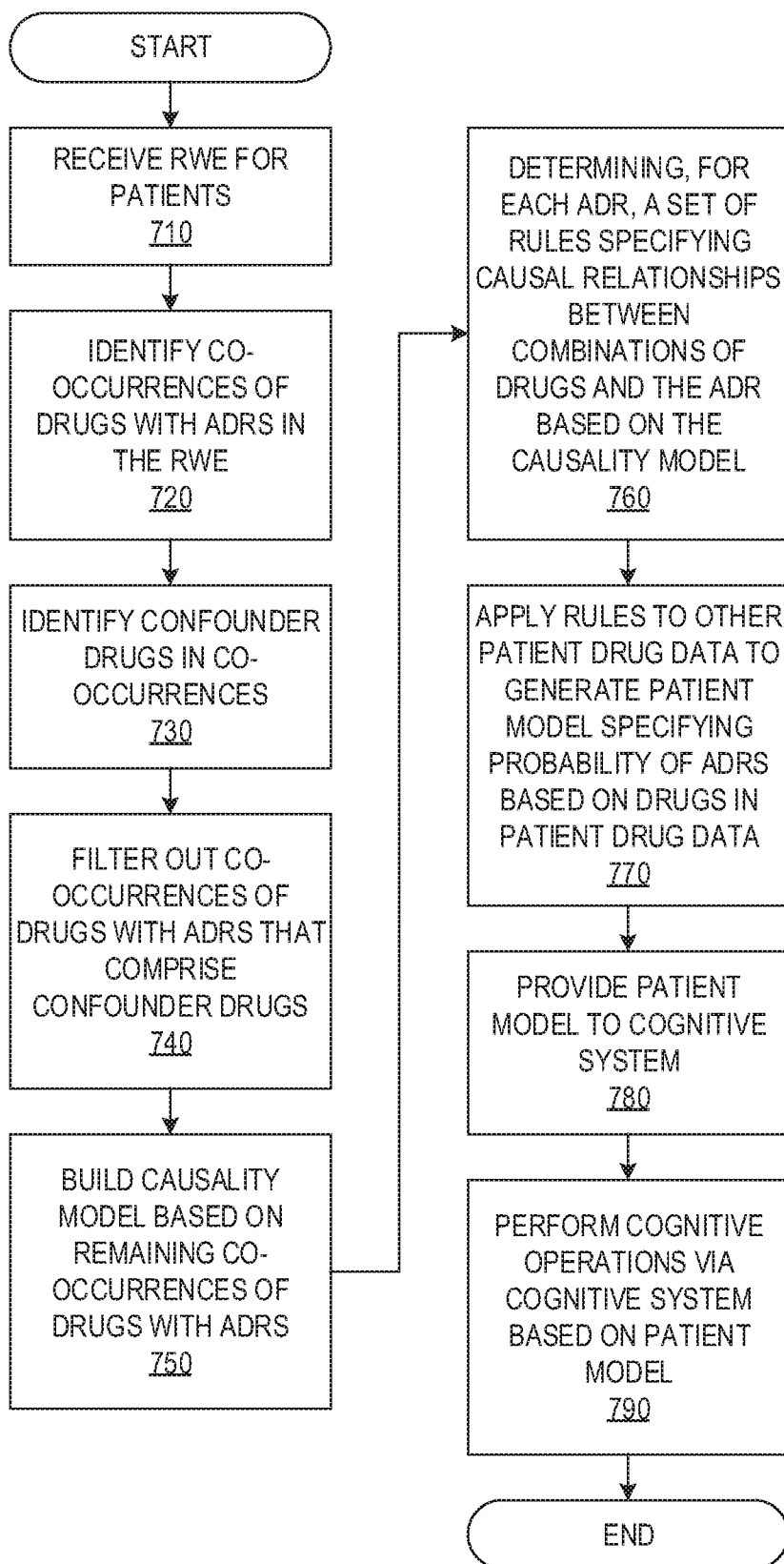
FIG. 7 is a flowchart outlining an example operation for learning multiple drug pattern relationships with adverse drug reactions and filtering out confounder drugs in accordance with one illustrative embodiment.

FIG. 7 is a flowchart outlining an example operation for learning multiple drug pattern relationships with adverse drug reactions and filtering out confounder drugs in accordance with one illustrative embodiment. As shown in FIG. 7, the operation starts by receiving real world evidence (RWE) for a plurality of patients (step 710). Co-occurrences of drugs with ADRs are identified in the RWE (step 720), which may involve applying knowledge obtained from various resource data structures from various resource information sources and may involve various operations, such as various natural language processing operations, as previously detailed above.

Confounder drugs in the identified co-occurrences are identified (step 730). As noted above, this may involve a process of evaluating improvement scores and comparisons to thresholds to determine if combinations of drugs have a significant improvement over sub-combinations within these combinations, e.g., adding drug C to the sub-combination AB results in a significant enough improvement in the association of ABC with the ADR of P than the association score of AB to P. If it does not, then C is most likely a confounder drug. Co-occurrences that are determined to have confounder drugs present may be eliminated from further consideration, e.g., filtered out (step 740). Although filtered out, the confounder drugs may be identified to a reporting mechanism, such as common confounder logic 160 in FIG. 1, to report such confounders to cognitive systems, to resource information sources, or the like. A causality model is then built based on the remaining co-occurrences of drugs with ADRs and may be provided for use by a cognitive system (step 750). The operation may terminate at this point, however for purpose of completeness, the flowchart further illustrates the implementation of the causal model with the cognitive system to evaluate another patient.

Based on the causality model, for each ADR, a set of rules specifying causal relationships between combinations of drugs and the ADR are determined (step 760). The rules are applied to other patient drug data to generate a patient model for the other patient that specifies the probability of ADRs based on drugs in the patient drug data (step 770). The patient model may be provided to a cognitive system (step 780) which performs cognitive operations, e.g., treatment recommendation operations, based on the patient model, e.g., based on the probabilities of ADRs associated with the patient due to the drugs being taken by the patient as indicated by the causal model built by the mechanisms of the illustrative embodiments (step 790). The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a framework for learning multiple drug-adverse drug reaction associations and predicting patient adverse drug reactions (ADRs), the method comprising:

executing, by a co-occurrence logic module of the framework, computer natural language processing logic on real world evidence comprising patient electronic medical record (EMR) data and ADR data, to extract features, from natural language content of the real world evidence, specifying co-occurrences of first features referencing drugs with second features referencing adverse drug reactions;

generating, by the co-occurrence logic module, one or more drug-ADR rules, based on the extracted first features and second features, specifying multiple drug-ADR relationships, wherein each of the one or more drug-ADR rules specifies a corresponding drug pattern comprising a plurality of drugs and corresponding adverse drug reaction;

filtering, by a confounder filter logic module of the framework, the one or more drug-ADR rules to remove a subset of one or more drug-ADR rules having confounder drugs specified in the subset of drug-ADR rules, and thereby generate a filtered set of drug-ADR rules wherein filtering the one or more drug-ADR rules further comprises:

calculating, for a first drug-ADR rule of the one or more drug-ADR rules, an improvement metric specifying an amount of improvement of a corresponding association score for the first drug-ADR rule over an association score for another second drug-ADR rule specifying a sub-pattern of the corresponding drug pattern of the first drug-ADR rule and the corresponding adverse drug reaction of the first drug-ADR rule; and determining, for the first drug-ADR rule, whether to maintain the first drug-ADR rule or remove the first drug-ADR rule based on a value of the improvement metric;

generating, by a causal association logic module of the framework, a computer executed causal model based on the filtered set of drug-ADR rules, wherein the computer executed causal model comprises, for each ADR in a set of ADRs, a corresponding set of one or more computer executed rules, each computer executed rule specifying one or more drugs having a causal relationship with the ADR which is executed on other patient EMR data, wherein generating the causal model based on the filtered set of drug-ADR rules further comprises, for each ADR:

generating a directed acyclic graph data structure in a Bayesian learning framework, wherein the directed acyclic graph data structure represents each drug pattern of each of the drug-ADR rules, in the filtered set of drug-ADR rules associated with the ADR, as a variable of the directed acyclic graph data structure;

determining transition probabilities for transitions between variables specified in the directed acyclic graph data structure;

determining causal relationships among one or more drug patterns, represented by the variables, and the ADR based on the directed acyclic graph data structure and the transition probabilities; and generating, for the ADR, the corresponding set of one or more rules based on the determined causal relationships;

evaluating other patient EMR data by applying the computer executed causal model to drug history data present in the other patient EMR data to identify probabilities of a patient encountering one or more ADRs in a set of ADRs; and generating, for the patient, a patient model based on the identified probabilities of the patient encountering one or more ADRs in the set of ADRs.

2. The method of claim 1, wherein executing computer natural language processing logic on the real world evidence comprises:

generating the one or more drug-ADR rules based on the identified co-occurrences, wherein each drug-ADR rule specifies a drug pattern identifying a plurality of drugs and a corresponding ADR; and selecting a sub-set of the one or more drug-ADR rules as a basis for generating the computer executed causal model based on at least one of a support metric or a confidence metric, wherein the support metric measures, for an associated drug-ADR rule, a number of instances of the co-occurrence in the real world evidence, and wherein the confidence metric measures, for an associated drug-ADR rule, a probability of the associated ADR given the drugs in the drug pattern of the associated drug-ADR rule.

3. The method of claim 2, wherein identifying all co-occurrences of references to drugs with reference to ADRs in the real world evidence comprises:

performing natural language processing of the real world evidence to identify at least one of terms, phrases, or medical codes identifying references to drugs and references to ADRs;

evaluating relative distances within the real world evidence, between each identified term, phrase or medical code identifying references to drugs and references to ADRs; and identifying co-occurrences based on the relative distances.

4. The method of claim 2, wherein selecting a sub-set of the one or more drug-ADR rules comprises, for each drug-ADR rule:

generating a contingency table data structure, where each entry in the contingency table data structure comprises a number of patient electronic medical records that satisfy a condition of the row and column of the contingency table data structure corresponding to the entry, wherein:

a first row of the contingency table data structure corresponds to patient electronic medical records that contain all drugs in the drug pattern of the drug-ADR rule, a second row of the contingency table data structure corresponds to patient electronic medical records that contain none of the drugs in the drug pattern of the drug-ADR rule, a first column of the contingency table data structure corresponds to the patient electronic medical records that contain the ADR in the drug-ADR rule, and a second column of the contingency table data structure corresponds to the patient electronic medical records that do not contain the ADR in the drug-ADR rule.

5. The method of claim 1, further comprising:

identifying one or more confounder drugs present in the subset of one or more drug-ADR rules having confounder drugs; and updating a confounder drug resource information data source based on the identified one or more confounder drugs.

6. The method of claim 1, further comprising:

configuring a cognitive computing system to modify logic of the cognitive computing system to implement the computer executed causal model; and executing, by the cognitive computing system, an automated treatment recommendation operation that provides a treatment recommendation output to a computing device associated with a medical practitioner based on the patient model, wherein determining, for the first drug-ADR rule, whether to maintain the first drug-ADR rule or remove the first drug-ADR rule based on a value of the improvement metric further comprises:

comparing the improvement metric corresponding to the first drug-ADR rule to an improvement metric threshold value;

in response to the improvement metric corresponding to the first drug-ADR rule not being equal to or greater than the improvement metric threshold value, determining that a confounder drug is present in the corresponding drug pattern of the first drug-ADR rule; and identifying the confounder drug in the corresponding drug pattern based on a difference between the corresponding drug pattern and the sub-pattern.

7. A computer program product comprising a computer readable storage medium having a computer readable program stored therein, wherein the computer readable program, when executed on a computing device, causes the computing device to:

execute, by a co-occurrence logic module executing on the computing device, computer natural language processing logic on real world evidence comprising patient electronic medical record (EMR) data and adverse drug reaction (ADR) data, to extract features, from natural language content of the real world evidence, specifying co-occurrences of first features referencing drugs with second features referencing adverse drug reactions;

generate, by the co-occurrence logic module, one or more drug-ADR rules, based on the extracted first features and second features, specifying multiple drug-ADR relationships, wherein each of the one or more drug-ADR rules specifies a corresponding drug pattern comprising a plurality of drugs and corresponding adverse drug reaction;

filter, by a confounder filter logic module on the computing device, the one or more drug-ADR rules to remove a subset of one or more drug-ADR rules having confounder drugs specified in the subset of drug-ADR rules, and thereby generate a filtered set of drug-ADR rules, wherein the computer readable program to filter the one or more drug-ADR rules further causes the computing device to:

calculate, for a first drug-ADR rule of the one or more drug-ADR rules, an improvement metric specifying an amount of improvement of a corresponding association score for the first drug-ADR rule over an association score for another second drug-ADR rule specifying a sub-pattern of the corresponding drug pattern of the first drug-ADR rule and the corresponding adverse drug reaction of the first drug-ADR rule; and determine, for each first drug-ADR rule, whether to maintain the first drug-ADR rule or remove the first drug-ADR rule based on a value of the improvement metric;

generate, by a causal association logic module on the computing device, a computer executed causal model based on the filtered set of drug-ADR rules, wherein the computer executed causal model comprises, for each ADR in a set of ADRs, a corresponding set of one or more computer executed rules, each computer executed rule specifying one or more drugs having a causal relationship with the ADR which is executed on other patient EMR data, wherein generating the causal model based on the filtered set of drug-ADR rules further comprises, for each ADR:

generating a directed acyclic graph data structure in a Bayesian learning framework, wherein the directed acyclic graph data structure represents each drug pattern of each of the drug-ADR rules, in the filtered set of drug-ADR rules associated with the ADR, as a variable of the directed acyclic graph data structure;

determining transition probabilities for transitions between variables specified in the directed acyclic graph data structure;

determining causal relationships among one or more drug patterns, represented by the variables, and the ADR based on the directed acyclic graph data structure and the transition probabilities; and generating, for the ADR, the corresponding set of one or more rules based on the determined causal relationships;

evaluate other patient EMR data by applying the computer executed causal model to drug history data present in the other patient EMR data to identify probabilities of a patient encountering one or more ADRs in a set of ADRs; and generate, for the patient, a patient model based on the identified probabilities of the patient encountering one or more ADRs in the set of ADRs.

8. The computer program product of claim 7, wherein the computer readable program further causes the computing device to execute computer natural language processing logic on the real world evidence at least by:

generating the one or more drug-ADR rules based on the identified co-occurrences, wherein each drug-ADR rule specifies a drug pattern identifying a plurality of drugs and a corresponding ADR; and selecting a sub-set of the one or more drug-ADR rules as a basis for generating the computer executed causal model based on at least one of a support metric or a confidence metric, wherein the support metric measures, for an associated drug-ADR rule, a number of instances of the co-occurrence in the real world evidence, and wherein the confidence metric measures, for an associated drug-ADR rule, a probability of the associated ADR given the drugs in the drug pattern of the associated drug-ADR rule.

9. The computer program product of claim 8, wherein the computer readable program further causes the computing device to identify all co-occurrences of references to drugs with reference to ADRs in the real world evidence at least by:
performing natural language processing of the real world evidence to identify at least one of terms, phrases, or medical codes identifying references to drugs and references to ADRs;
evaluating relative distances within the real world evidence, between each identified term, phrase or medical code identifying references to drugs and references to ADRs; and
identifying co-occurrences based on the relative distances.

10. The computer program product of claim 8, wherein the computer readable program further causes the computing device to select a sub-set of the one or more drug-ADR rules at least by, for each drug-ADR rule:
generating a contingency table data structure, where each entry in the contingency table data structure comprises a number of patient electronic medical records that satisfy a condition of the row and column of the contingency table data structure corresponding to the entry, wherein:
a first row of the contingency table data structure corresponds to patient electronic medical records that contain all drugs in the drug pattern of the drug-ADR rule,
a second row of the contingency table data structure corresponds to patient electronic medical records that contain none of the drugs in the drug pattern of the drug-ADR rule,
a first column of the contingency table data structure corresponds to the patient electronic medical records that contain the ADR in the drug-ADR rule, and
a second column of the contingency table data structure corresponds to the patient electronic medical records that do not contain the ADR in the drug-ADR rule.

11. The computer program product of claim 7, wherein the computer readable program further causes the computing device to:
identify one or more confounder drugs present in the subset of one or more drug-ADR rules having confounder drugs; and
update a confounder drug resource information data source based on the identified one or more confounder drugs.

12. The computer program product of claim 7, wherein the computer readable program further causes the computing device to:
configure a cognitive computing system to modify logic of the cognitive computing system to implement the computer executed causal model; and
execute, by the cognitive computing system, an automated treatment recommendation operation that provides a treatment recommendation output to a computing device associated with a medical practitioner based on the patient model, wherein determining, for the first drug-ADR rule, whether to maintain the first drug-ADR rule or remove the first drug-ADR rule based on a value of the improvement metric further comprises:

comparing the improvement metric corresponding to the first drug-ADR rule to an improvement metric threshold value;
in response to the improvement metric corresponding to the first drug-ADR rule not being equal to or greater than the improvement metric threshold value, determining that a confounder drug is present in the corresponding drug pattern of the first drug-ADR rule; and
identifying the confounder drug in the corresponding drug pattern based on a difference between the corresponding drug pattern and the sub-pattern.

13. An apparatus comprising:
at least one processor; and
at least one memory coupled to the at least one processor, wherein the at least one memory comprises instructions which, when executed by the at least one processor, cause the at least one processor to implement a framework for learning multiple drug-adverse drug reaction associations, which operates to:
execute, by a co-occurrence logic module executing on the computing device, computer natural language processing logic on real world evidence comprising patient electronic medical record (EMR) data and adverse drug reaction (ADR) data, to extract features, from natural language content of the real world evidence, specifying co-occurrences of first features referencing drugs with second features referencing adverse drug reactions;
generate, by the co-occurrence logic module, one or more drug-ADR rules, based on the extracted first features and second features, specifying multiple drug-ADR relationships, wherein each of the one or more drug-ADR rules specifies a corresponding drug pattern comprising a plurality of drugs and corresponding adverse drug reaction;
filter, by a confounder filter logic module on the computing device, the one or more drug-ADR rules to remove a subset of one or more drug-ADR rules having confounder drugs specified in the subset of drug-ADR rules, and thereby generate a filtered set of drug-ADR rules, wherein the instructions to filter the one or more drug-ADR rules further causes the computing device to:
calculate, for a first drug-ADR rule of the one or more drug-ADR rules, an improvement metric specifying an amount of improvement of a corresponding association score for the first drug-ADR rule over an association score for another second drug-ADR rule specifying a sub-pattern of the corresponding drug pattern of the first drug-ADR rule and the corresponding adverse drug reaction of the first drug-ADR rule; and
determine, for each first drug-ADR rule, whether to maintain the first drug-ADR rule or remove the first drug-ADR rule based on a value of the improvement metric;
generate, by a causal association logic module of the framework, a computer executed causal model based on the filtered set of drug-ADR rules, wherein the computer executed causal model comprises, for each ADR in a set of ADRs, a corresponding set of one or more computer executed rules, each computer executed rule specifying one or more drugs having a causal relationship with the ADR which is executed on other patient EMR data, wherein generating the causal model based on the filtered set of drug-ADR rules further comprises, for each ADR:

generating a directed acyclic graph data structure in a Bayesian learning framework, wherein the directed acyclic graph data structure represents each drug pattern of each of the drug-ADR rules, in the filtered set of drug-ADR rules associated with the ADR, as a variable of the directed acyclic graph data structure;

determining transition probabilities for transitions between variables specified in the directed acyclic graph data structure;

determining causal relationships among one or more drug patterns, represented by the variables, and the ADR based on the directed acyclic graph data structure and the transition probabilities; and generating, for the ADR, the corresponding set of one or more rules based on the determined causal relationships;

evaluate other patient EMR data by applying the computer executed causal model to drug history data present in the other patient EMR data to identify probabilities of a patient encountering one or more ADRs in a set of ADRs; and generate, for the patient, a patient model based on the identified probabilities of the patient encountering one or more ADRs in the set of ADRs.

14. The apparatus of claim 13, wherein the instructions further cause the at least one processor to:

configure a cognitive computing system to modify logic of the cognitive computing system to implement the computer executed causal model; and execute, by the cognitive computing system, an automated treatment recommendation operation that provides a treatment recommendation output to a computing device associated with a medical practitioner based on the patient model, wherein determining, for the first drug-ADR rule, whether to maintain the first drug-ADR rule or remove the first drug-ADR rule based on a value of the improvement metric further comprises:

comparing the improvement metric corresponding to the first drug-ADR rule to an improvement metric threshold value;

in response to the improvement metric corresponding to the first drug-ADR rule not being equal to or greater than the improvement metric threshold value, determining that a confounder drug is present in the corresponding drug pattern of the first drug-ADR rule; and identifying the confounder drug in the corresponding drug pattern based on a difference between the corresponding drug pattern and the sub-pattern.

* * * * *